US011045456B2

(12) United States Patent
Li

(10) Patent No.: US 11,045,456 B2
(45) Date of Patent: Jun. 29, 2021

(54) COMPOSITIONS AND METHODS FOR TREATING COPD AND OTHER INFLAMMATORY CONDITIONS

(71) Applicant: Georgia State University Research Foundation, Inc., Atlanta, GA (US)

(72) Inventor: Jian-Dong Li, Marietta, GA (US)

(73) Assignee: Georgia State University Research Foundation, Inc., Atlanta, GA (US)

( * ) Notice: Subject to any disclaimer, the term of this patent is extended or adjusted under 35 U.S.C. 154(b) by 0 days.

(21) Appl. No.: 15/559,728

(22) PCT Filed: Mar. 21, 2016

(86) PCT No.: PCT/US2016/023475
§ 371 (c)(1),
(2) Date: Sep. 19, 2017

(87) PCT Pub. No.: WO2016/154143
PCT Pub. Date: Sep. 29, 2016

(65) Prior Publication Data
US 2018/0042904 A1    Feb. 15, 2018

Related U.S. Application Data

(60) Provisional application No. 62/136,115, filed on Mar. 20, 2015.

(51) Int. Cl.
A61K 31/44      (2006.01)
A61K 31/423     (2006.01)
A61K 45/06      (2006.01)
A61P 11/00      (2006.01)
A61K 9/00       (2006.01)
A61K 31/12      (2006.01)
A61K 31/573     (2006.01)
A61K 31/7088    (2006.01)
C12N 9/16       (2006.01)
A61K 9/70       (2006.01)
A61K 35/74      (2015.01)

(52) U.S. Cl.
CPC ............ *A61K 31/44* (2013.01); *A61K 9/0053* (2013.01); *A61K 9/0073* (2013.01); *A61K 9/7023* (2013.01); *A61K 31/12* (2013.01); *A61K 31/423* (2013.01); *A61K 31/573* (2013.01); *A61K 31/7088* (2013.01); *A61K 35/74* (2013.01); *A61K 45/06* (2013.01); *A61P 11/00* (2018.01); *C12N 9/16* (2013.01); *C12Y 301/04053* (2013.01)

(58) Field of Classification Search
None
See application file for complete search history.

(56) References Cited

U.S. PATENT DOCUMENTS

2012/0040956 A1    2/2012   Wabnitz et al.
2013/0172303 A1    7/2013   Freire et al.

FOREIGN PATENT DOCUMENTS

CA     2536738          3/2005
WO     2007108750       9/2007
WO     2008070616       6/2008
WO     2013/155123      10/2013
WO     WO-2013155123 A1 * 10/2013 ............. A61K 31/44

OTHER PUBLICATIONS

King et al. "Bacteria in COPD; their potential role and treatment." Translational Respiratory Medicine 1.1 (2013): 13. (Year: 2013).*
Antonela, "New Therapeutic Options in the Management of COPD-Focus on Roflumilast", International Journal of Chronic Obstructive Pulmonary Disease, vol. 6, 2011, pp. 147-155.
Bora et al., "A Reporter Gene Assay for Screening of PDE4 Subtype Selective Inhibitors", Biochemical and Biophysical Research Communications, vol. 356, No. 1, Mar. 17, 2007, pp. 153-158.
Cullen et al., "Investigation of the alkenyldiarylmethane non-nucleoside reverse transcriptase inhibitors as potential cAMP phosphodiesterase-482 inhibitors", Bioorganic & Medicinal Chemistry Letters, Pergamon, Amsterdam, NL, vol. 18, Issue No. 4, Dec. 14, 2007, pp. 1530-1533.
Milara et al., "Roflumilast Improves Corticosteroid Resistance COPD Bronchial Epithelial Cells Stimulated with Toll Like Receptor 3 Agonist", Respiratory Research, vol. 16, No. 1, Feb. 5, 2015, 12 pages.
Moghaddam et al., "Curcumin Inhibits COPD-like Airway Inflammation and Lung Cancer Progression in Mice", Carcinogenesis (Oxford), vol. 30, No. 11, Nov. 11, 2009, pp. 1949-1956.
Narayanan et al., "OCID 2987: A Novel, Chemically Distinct Orally Active PDE4 Inhibitor", Journal of Allergy and Clinical Immunology, Elsevier, vol. 125, No. 2, Supplement 1, Feb. 1, 2010, pp. AB49.

(Continued)

*Primary Examiner* — Emily A Cordas
(74) *Attorney, Agent, or Firm* — Kilpatrick Townsend & Stockton LLP

(57) ABSTRACT

The present invention features, inter alia, pharmaceutical compositions and their use in the preparation of a medicament (e.g., a medicament for inflammation, such as an inflammatory lung disease) or in a therapeutic regimen. The compositions can include at least two active agents: a first agent that inhibits PDE4 (e.g., roflumilast) and a second active agent that inhibits the expression or activity of one or more PDE4B variants (e.g., PDE4B2). The compositions and methods will attenuate an unwanted up-regulation of a PDE4B (e.g., PDE4B2) and may thereby improve treatment with the first agent (e.g., roflumilast). For example, the second agent may improve the efficacy of the first agent, decrease the effective dose of the first agent, ameliorate the tolerance to the first agent that would otherwise develop (e.g., in patients with COPD exacerbation), reduce unwanted side effects caused by the first agent, or otherwise improve treatment regimes including a PDE4 inhibitor.

11 Claims, 7 Drawing Sheets

Specification includes a Sequence Listing.

(56) References Cited

OTHER PUBLICATIONS

Tannheimer et al., "Additive Anti-inflammatory Effects of Beta 2 Adrenoceptor Agonists or Glucocorticosteroid with Roflumilast in Human Peripheral Blood Mononuclear Cells", Pulmornary Pharmacology & Therapeutics, Academic Press, vol. 25, No. 2, Jan. 13, 2012, pp. 178-184.

Dong Meng, "MEK1 Binds BetaarrestinI Directly, Influencing Both its Phosphorylation by ERK and the Timing of its Isoprenaline-stimulated Internalization," pp. 1-219 (2009) via http://theses.gla.ac.uk/1614/1/2009mengphd.pdf.

Gobejishvili et al., "S-Adenosylmethionine Decreases Lipopolysaccharide-induced Phosphodiesterase 4B2 and Attenuates Tumor Necrosis Factor Expression via cAMP/Protein Kinase A Pathway," *J. Pharmocol. Exp. Ther.*, 337(2):433-443 (2011).

Sakamoto et al., "Synthesis and Anti-HIV Activity of New Metabolically Stable Alkenyldiarylmethane Non-Nucleoside Reverse Transcriptase Inhibitors Incorporating N-Methoxy Imidoyl Halide and 1,2,4-Oxadiazole Systems," *J. Med. Chem.*, 50(14):3314-3321 (2007).

Komatsu et al. "Inhibition of PDE4B suppresses inflammation by increasing expression of the deubiquitinase CYLD" Nat. Commun., 2013, vol. 4, Issue 1684.

Barber et al. "Differential expression of PDE4 cAMP phosphodiesterase isoforms in inflammatory cells of smokers with COPD, smokers without COPD, and nonsmokers," Am. J. Physiol. Lung Cell Mol. Physiol., 2004, vol. 287, pp. L332-L343.

Donnell, et al. "Identification of pyridazino [4, 5-b] indolizines as selective PDE4B inhibitors" Bioorganic & Medicinal Chemistry Letters 20 (2010) 2163-2167. 5 pages.

Yu, et al. "Development of Inhibitors Targeting Hypoxia-Inducible Factor 1 and 2 for Cancer Therapy" Yonsei Medical Journal plssN:0513-5796 elssn: 1976-2437. 8 pages.

Hagen, et al. "Discovery of Triazines as selective PDE4B verses PDE4D inhibitors." Bioorganic & Medicinal Chemistry Letters 24 (2014) 4031-4034. 4 pages.

Naganuma, et al. "Discovery of selective PDE4B inhibitors." Bioorganic & Medicinal Chemistry Letters 19 (2009) 3174-3176.

Cullen et al., "Investigation of the Alkenyldiarylmethane Non-Nucleoside Reverse Transcriptase Inhibitors as Potential Camp Phosphodiesterase-4B2 Inhibitors", Bioorganic & Medicinal Chemistry Letters, vol. 18, Issue 4, 2008, pp. 1530-1533.

Wu, et al., Continuing Medical Education Courses, Respiratory Medicine, Military Medical Science Press, pp. 462-464, Oct. 13, 2020.

* cited by examiner

Figs. 2A-I

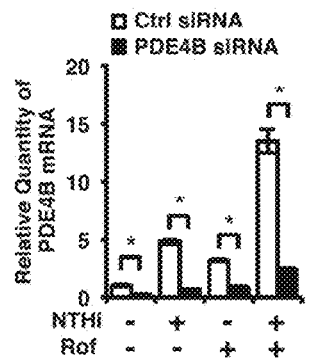
Fig. 3
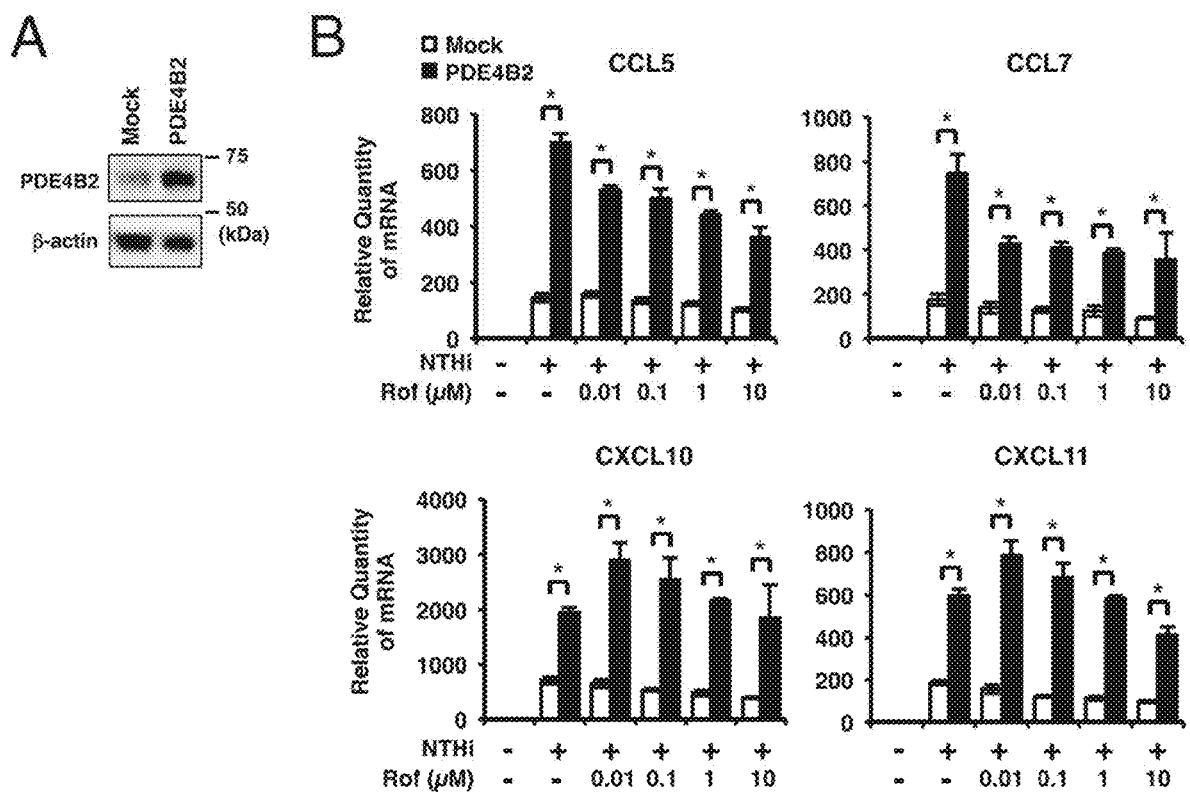
Figs. 4A-B

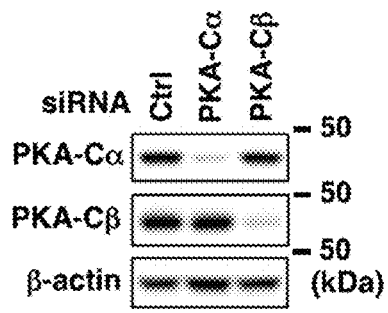
Fig. 5
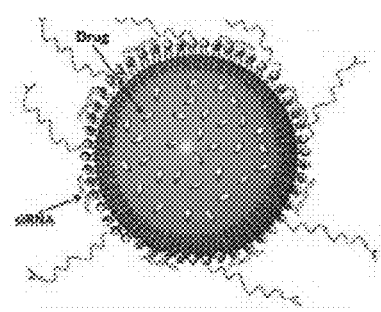
Fig. 6
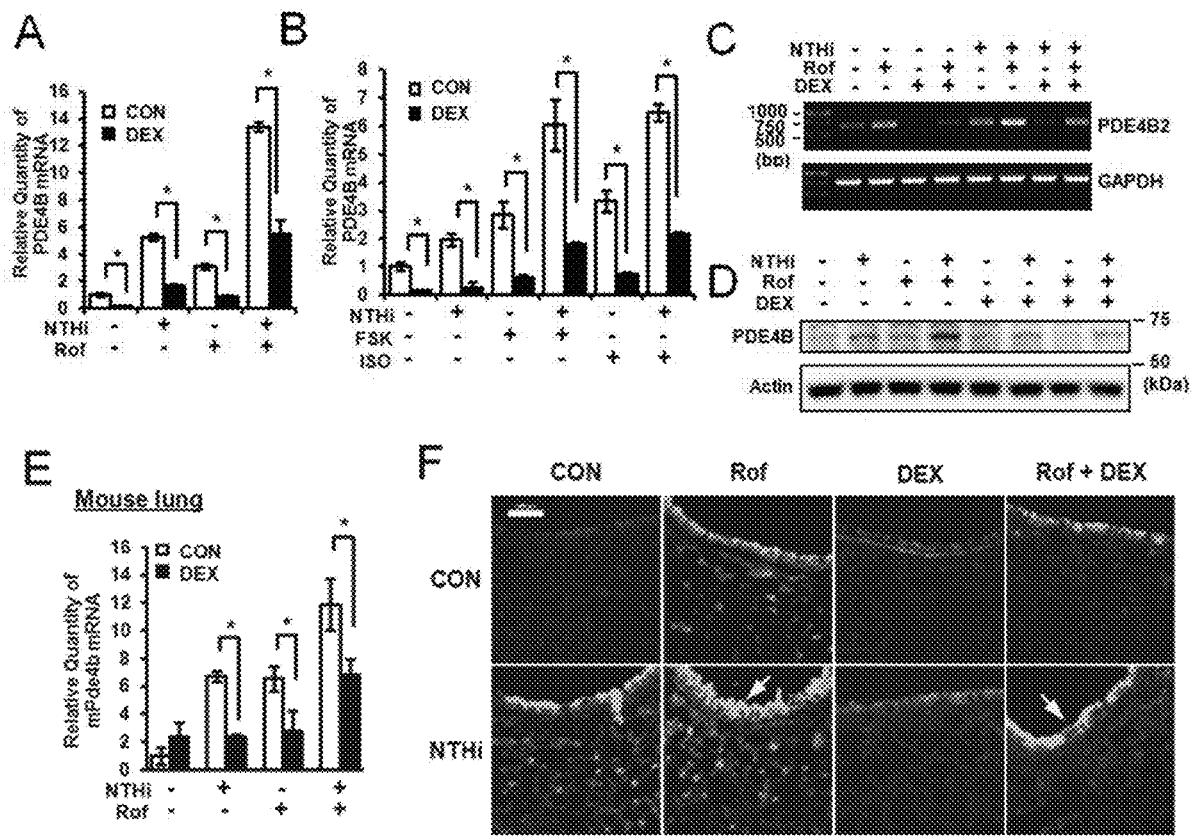
Figs. 7A-F

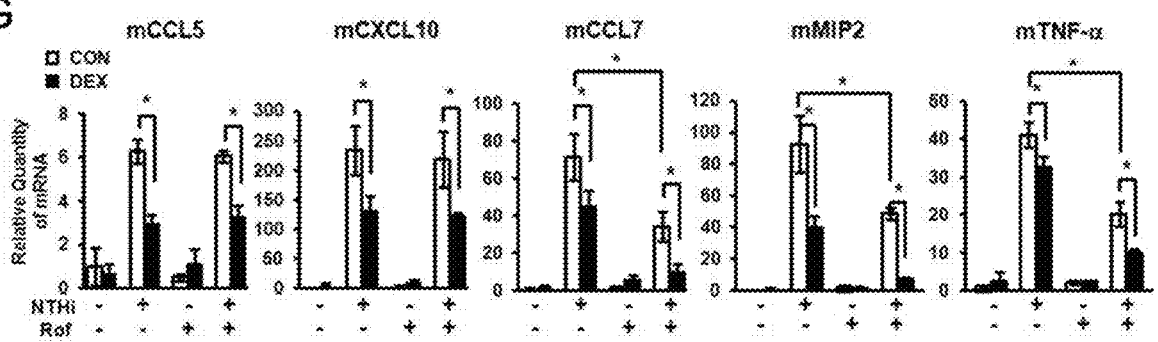
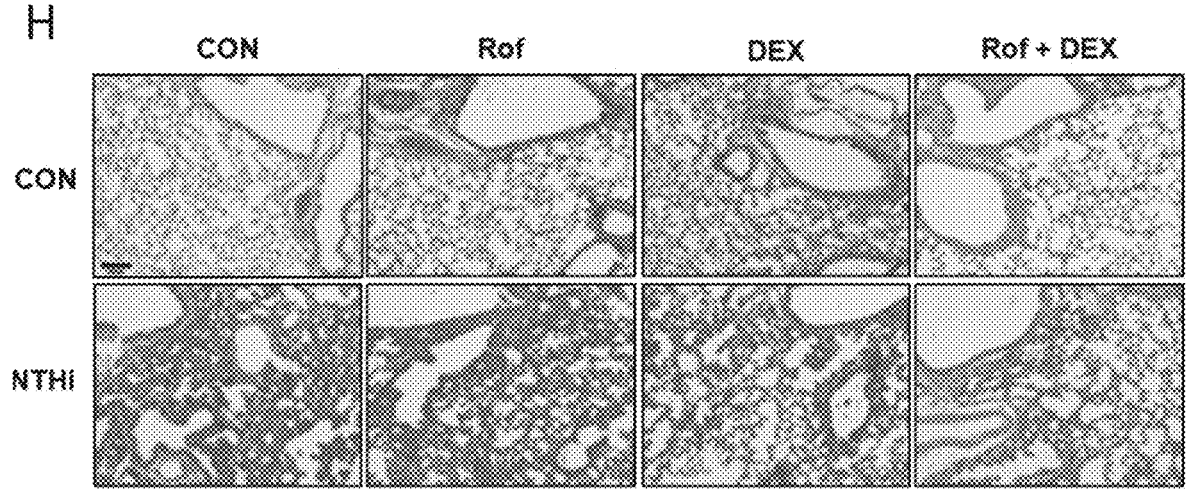
Figs. 7G-H

SEQUENCE LISTING

<160> NUMBER OF SEQ ID NOS: 41

<210> SEQ ID NO 1
<211> LENGTH: 1668
<212> TYPE: DNA
<213> ORGANISM: Homo sapiens

<400> SEQUENCE: 1
tccctgggag agactgacat agacattgca acagaagaca agtcccccgt ggatacataa    60

| | |
|---|---|
| tccccctctc cctgtggaga tgaacattct atccttgatg agcatgccag ctatgtggta | 120 |
| gggccagccc accatggggg ccaagacctg cacaggacaa gggccacctg gcctttcagt | 180 |
| tacttgagtt tggagtcaga aagcaagacc aggaagcaaa tagcagctca ggaaatccca | 240 |
| cggttgactt gccttgatgg caagcttggt ggagagggct gaagctgttg ctggggccg | 300 |
| attctgatca agacacatgg cttgaaaatg aagacacaa aactgagaga tcattctgca | 360 |
| ctaagtttcg ggaacttatc cccgacagtg actgaactca ctgactaata acttcattta | 420 |
| tgaatcttct cacttgtccc tttgtctgcc aacctgtgtg cctttttgt aaaacatttt | 480 |
| catgtcttta aaatgcctgt tgaatacctg gagtttagta tcaacttcta cacagataag | 540 |
| ctttcaaagt tgacaaactt ttttgactct ttctggaaaa gggaagaaa atagtcttcc | 600 |
| ttctttcttg ggcaatatcc ttcactttac tacagttact tttgcaaaca gacagaaagg | 660 |
| atacacttct aaccacattt tacttccttc ccctgttgtc cagtccaact ccacagtcac | 720 |
| tcttaaaact tctctctgtt tgcctgcctc aacagtact tttaacttt tgctgtaaac | 780 |
| agaataaaat tgaacaaatt aggggtaga aaggagcagt ggtgtcgttc accgtgagag | 840 |
| tctgcataga actcagcagt gtgccctgct gtgtcttgga ccctgcccc cacaggagtt | 900 |
| gctacagtcc ctggccctgc ttcccatcct cctctcttca cccgttagc tgttttcaat | 960 |
| gtaatgctgc cgtccttctc ttgcactgcc ttctgcgcta acacctccat tcctgtttat | 1020 |
| aaccgtgtat ttattactta atgtatataa tgtaatgttt tgtaagttat taatttatat | 1080 |
| atctaacatt gcctgccaat ggtggtgtta aatttgtgta gaaaactctg cctaagagtt | 1140 |
| acgactttt cttgtaatgt tttgtattgt gtattatata acccaaacgt cacttagtag | 1200 |
| agacatatgg ccccttggc agagaggaca ggggtgggct tttgttcaaa gggtctgccc | 1260 |
| tttccctgcc tgagttgcta cttctgcaca accccttat gaaccagttt tggaaacaat | 1320 |
| attctcacat tagatactaa atggtttata ctgagtcttt tacttttgta tagcttgata | 1380 |
| ggggcagggg caatgggatg tagttttac ccaggttcta tccaaatcta tgtgggcatg | 1440 |
| agttgggtta taactggatc ctactatcat tgtggctttg gttcaaaagg aaacactaca | 1500 |
| tttgctcaca gatgattctt ctgattcttc tgaatgctcc cgaactactg actttgaaga | 1560 |
| ggtagcctcc tgcctgccat taagcaggaa tgtcatgttc cagttcatta caaaagaaaa | 1620 |
| caataaaaca atgtgaattt ttataataaa aaaaaaaaa aggaattc | 1668 |

<210> SEQ ID NO 2
<211> LENGTH: 3884
<212> TYPE: DNA
<213> ORGANISM: Homo sapiens

<400> SEQUENCE: 2

| | |
|---|---|
| atcacatacc ctaaagaacc ctgggatgac taaggcagag agagtctgag aaaactcttt | 60 |
| ggtgcttctg cctttagttt taggacacat ttatgcagat gagcttataa gagaccgttc | 120 |
| cctccgcctt cttcctcaga ggaagtttct tggtagatca ccgacacctc atccaggcgg | 180 |
| ggggttgggg ggaaacttgg caccagccat cccaggcaga gcaccactgt gatttgttct | 240 |
| cctggtggag agagctggaa ggaaggagcc agcgtgcaaa taatgaagga gcacgggggc | 300 |
| accttcagta gcaccggaat cagcggtggt agcggtgact ctgctatgga cagcctgcag | 360 |
| ccgctccagc ctaactacat gcctgtgtgt ttgtttgcag aagaatctta tcaaaaatta | 420 |
| gcaatggaaa cgctggagga attagactgg tgtttagacc agctagagac catacagacc | 480 |
| taccggtctg tcagtgagat ggcttctaac aagttcaaaa gaatgctgaa ccgggagctg | 540 |

-continued

| | | | | |
|---|---|---|---|---|
| acacacctct | cagagatgag | ccgatcaggg | aaccaggtgt | ctgaatacat ttcaaatact | 600 |
| ttcttagaca | agcagaatga | tgtggagatc | ccatctccta | cccagaaaga cagggagaaa | 660 |
| aagaaaaagc | agcagctcat | gacccagata | agtggagtga | agaaattaat gcatagttca | 720 |
| agcctaaaca | atacaagcat | ctcacgcttt | ggagtcaaca | ctgaaaatga agatcacctg | 780 |
| gccaaggagc | tggaagacct | gaacaaatgg | ggtcttaaca | tctttaatgt ggctggatat | 840 |
| tctcacaata | gacccctaac | atgcatcatg | tatgctatat | ccaggaaag agacctccta | 900 |
| aagacattca | gaatctcatc | tgacacattt | ataacctaca | tgatgacttt agaagaccat | 960 |
| taccattctg | acgtggcata | tcacaacagc | ctgcacgctg | ctgatgtagc ccagtcgacc | 1020 |
| catgttctcc | tttctacacc | agcattagac | gctgtcttca | cagatttgga gatcctggct | 1080 |
| gccattttg | cagctgccat | ccatgacgtt | gatcatcctg | gagtctccaa tcagtttctc | 1140 |
| atcaacacaa | attcagaact | tgctttgatg | tataatgatg | aatctgtgtt ggaaaatcat | 1200 |
| caccttgctg | tgggtttcaa | actgctgcaa | gaagaacact | gtgacatctt catgaatctc | 1260 |
| accaagaagc | agcgtcagac | actcaggaag | atggttattg | acatggtgtt agcaactgat | 1320 |
| atgtctaaac | atatgagcct | gctggcagac | ctgaagacaa | tggtagaaac gaagaaagtt | 1380 |
| acaagttcag | gcgttcttct | cctagacaac | tataccgatc | gcattcaggt ccttcgcaac | 1440 |
| atggtacact | gtgcagacct | gagcaacccc | accaagtcct | tggaattgta tcggcaatgg | 1500 |
| acagaccgca | tcatggagga | attttttccag | cagggagaca | aagagcggga gaggggaatg | 1560 |
| gaaattagcc | caatgtgtga | taaacacaca | gcttctgtgg | aaaaatccca ggttggtttc | 1620 |
| atcgactaca | ttgtccatcc | attgtgggag | acatgggcag | atttggtaca gcctgatgct | 1680 |
| caggacattc | tcgatacctt | agaagataac | aggaactggt | atcagagcat gatacctcaa | 1740 |
| agtccctcac | caccactgga | cgagcagaac | agggactgcc | agggtctgat ggagaagttt | 1800 |
| cagtttgaac | tgactctcga | tgaggaagat | tctgaaggac | ctgagaagga gggagggga | 1860 |
| cacagctatt | tcagcagcac | aaagacgctt | tgtgtgattg | atccagaaaa cagagattcc | 1920 |
| ctggagaga | ctgacataga | cattgcaaca | gaagacaagt | cccccgtgga tacataatcc | 1980 |
| ccctctccct | gtggagatga | acattctatc | cttgatgagc | atgccagcta tgtggtaggg | 2040 |
| ccagcccacc | atgggggcca | agacctgcac | aggacaaggg | ccacctggcc tttcagttac | 2100 |
| ttgagtttgg | agtcagaaag | caagaccagg | aagcaaatag | cagctcagga aatcccacgg | 2160 |
| ttgacttgcc | ttgatggcaa | gcttggtgga | gagggctgaa | gctgttgctg ggggccgatt | 2220 |
| ctgatcaaga | cacatggctt | gaaaatggaa | gacacaaaac | tgagagatca ttctgcacta | 2280 |
| agtttcggga | acttatcccc | gacagtgact | gaactcactg | actaataact tcatttatga | 2340 |
| atcttctcac | ttgtcccttt | gtctgccaac | ctgtgtgcct | tttttgtaaa acattttcat | 2400 |
| gtctttaaaa | tgcctgttga | atacctggag | tttagtatca | acttctacac agataagctt | 2460 |
| tcaaagttga | caaacttttt | tgactctttc | tggaaaaggg | aaagaaaata gtcttccttc | 2520 |
| tttcttgggc | aatatccttc | actttactac | agttactttt | gcaaacagac agaaaggata | 2580 |
| cacttctaac | cacattttac | ttccttcccc | tgttgtccag | tccaactcca cagtcactct | 2640 |
| taaaacttct | ctctgtttgc | ctgcctccaa | cagtacttt | aacttttttgc tgtaaacaga | 2700 |
| ataaaattga | acaaattagg | gggtagaaag | gagcagtggt | gtcgttcacc gtgagagtct | 2760 |
| gcatagaact | cagcagtgtg | ccctgctgtg | tcttggaccc | tgccccccac aggagttgta | 2820 |
| cagtccctgg | ccctgttccc | tacctcctct | cttcaccccg | ttaggctgtt ttcaatgtaa | 2880 |

```
tgctgccgtc cttctcttgc actgccttct gcgctaacac ctccattcct gtttataacc    2940
gtgtatttat tacttaatgt atataatgta atgttttgta agttattaat ttatatatct    3000
aacattgcct gccaatggtg gtgttaaatt tgtgtagaaa actctgccta agagttacga    3060 cttttttcttg taatgttttg tattgtgtat tatataaccc aaacgtcact tagtagagac   3120
atatggcccc cttggcagag aggacagggg tgggcttttg ttcaaagggt ctgcccttc     3180 cctgcctgag ttgctacttc tgcacaaccc ctttatgaac cagttttgga aacaatattc    3240
tcacattaga tactaaatgg tttatactga gcttttactt ttgtatagct tgatagggc     3300 agggggcaat gggatgtagt ttttacccag gttctatcca aatctatgtg ggcatgagtt    3360
gggttataac tggatcctac tatcattgtg gctttggttc aaaaggaaac actacatttg    3420
ctcacagatg attcttctga atgctcccga actactgact ttgaagaggt agcctcctgc    3480
ctgccattaa gcaggaatgt catgttccag ttcattacaa aagaaaacaa taaaacaatg    3540
tgaattttta taataaaatg tgaactgatg tagcaaatta cgcaaatgtg aagcctcttc    3600
tgataacact tgttaggcct cttactgatg tcagtttcag tttgtaaaat atgtttcatg    3660
ctttcagttc agcattgtga ctcagtaatt acagaaaatg gcacaaatgt gcatgaccaa    3720
tgtatgtcta tgaacactgc attgtttcag gtggacattt tatcattttc aaatgtttct    3780
cacaatgtat gttatagtat tattattata tattgtgttc aaatgcattc taaagagact    3840
tttatatgag gtgaataaag aaaagcatga ttagattaaa aaaa                     3884

<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Thr Thr Tyr Ala Asp Phe Ile Ala Ser Gly Arg Thr Gly Arg Arg Asn
1               5                   10                  15

Ala Ile His Asp
            20

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      primerprimer

<400> SEQUENCE: 4
cgggtcctgg catcttgt                                                     18

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcagatgaaa aactgggaac ca                                                22

<210> SEQ ID NO 6
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tgtcggatta cgctggaggc                                                  20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
catcgtgtcc acagggatgc                                                  20

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ctataccgat cgcattcagg tc                                               22

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ctgtccattg ccgatacaat t                                                21

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gacttacccc tcgacaacca                                                  20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gaaagtctgc ctgccaagag                                                  20

<210> SEQ ID NO 12
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tgtgtgacaa gcacaatgct tcc                                               23

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cacgattgtc ctccaaagtg tcc                                               23

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ctacaccagt ggcaagtgc                                                    19

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ctttcgggtg acaaagacga c                                                 21

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ggcttgctca gccagttg                                                     18

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ggtggtcctt ctgtagctct c                                                 21

<210> SEQ ID NO 18
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 18
tcctgatttc tgcaagctct g                                              21

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gtccactctc aatcactctc ag                                             22

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gaaattattc ctgcaagcca attttg                                         26

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cccttctttt tcattgtagc aatg                                           24

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
attgtgtgct acagttgttc aag                                            23

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tttctcaata tctgccactt tcac                                           24

<210> SEQ ID NO 24
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 24
cccaggcagt cagatcatct t                                              21

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
agctgcccct cagcttga                                                  18

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
aacagtagaa gtcatctcag aaatgtttg                                      29

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gctggccatc atggtcaag                                                 19

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
acccagaaga ctgtggatgg                                                20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ggatgcaggg atgatgttct                                                20

<210> SEQ ID NO 30
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 30
gtagaggcca gttcccatca                                                  20

<210> SEQ ID NO 31
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ccaacaccta gtgcagagc                                                   19

<210> SEQ ID NO 32
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
aaggctgggc tcatttg                                                     17

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gtgtggtggg ggactgag                                                    18

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
acctttcctg ggcacagcca c                                                21

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gcagcgtgca ggctgttgtg                                                  20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 36
agcggtggta gcggtgactc                                              20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gcagcgtgca ggctgttgtg                                              20

<210> SEQ ID NO 38
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ctccacgcag ttcaccaagg aac                                          23

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tgtgtcagct cccggttcag c                                            21

<210> SEQ ID NO 40
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
actgtgaatt ctttcaaagg gatttgtg                                     28

<210> SEQ ID NO 41
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
ggtctattgt gagaatatcc agccacat                                     28

COMPOSITIONS AND METHODS FOR TREATING COPD AND OTHER INFLAMMATORY CONDITIONS

CROSS-REFERENCE TO RELATED APPLICATIONS

This application is a U.S. National Stage Application of International Application No. PCT/US2016/023475, filed on Mar. 21, 2016, which claims the benefit of the filing date of U.S. Provisional Application No. 62/136,115, filed on Mar. 20, 2015. The entire content of each of the above-referenced applications is hereby incorporated herein by reference in its entirety.

STATEMENT REGARDING FEDERALLY FUNDED RESEARCH

This invention was made with government support under grant number DC005843 awarded by the National Institutes of Health. The government has certain rights in the invention.

REFERENCE TO A SUBMISSION OF A SEQUENCE LISTING AS A TEXT FILE

The Sequence Listing written in file 056777-001010US-1086163_SL.txt created on Apr. 21, 2021, 16,693 bytes, machine format IBM-PC, MS-Windows operating system, is hereby incorporated by reference in its entirety for all purposes

FIELD OF THE INVENTION

The present invention relates to compositions and methods that combine the use of at least two agents that inhibit phosphodiesterases in the family defined as Family 4 (PDE4) and, more specifically, to combination therapies that include compounds such as roflumilast and a second active agent that inhibits a PDE4 of the B sub-family (i.e., a PDE4B such as PDE4B2). The compositions and methods will attenuate an unwanted up-regulation of a PDE4B (e.g., PDE4B2) and may thereby improve treatment with the first agent (e.g., roflumilast). For example, the second agent may improve the efficacy of the first agent, decrease the effective dose of the first agent, ameliorate the tolerance to the first agent that would otherwise develop (e.g., in patients with COPD exacerbation), reduce unwanted side effects caused by the first agent, or otherwise improve treatment regimes including administration of a PDE4 inhibitor.

BACKGROUND

Phosphodiesterases (PDEs) are important enzymes because they hydrolyze and thereby inactivate the second messengers cAMP and cGMP (adenosine 3'5'-cyclic monophosphate and guanosine 3'5'-cyclic monophosphate, respectively). In addition to terminating the signals mediated by cAMP and cGMP, PDEs also play a vital role in intracellular localization of cyclic nucleotide signaling and integrate those pathways with other signaling pathways (for review, see Halpin, *Intl. J. of COPD* 3(4):543-561, 2008).

Over time, investigators have come to identify PDEs with different chromatographic and kinetic properties and different substrate specificity, which now constitute a super family of enzymes containing at least eleven families (PDE4-PDE11; Halpin, supra). In the human genome, at least 21 genes have been identified to date that encode PDEs, and many studies have focused on the physiochemical and regulatory properties of the encoded proteins (see, e.g., Conti and Jin, *Prog. Nucleic Acid Res. Mol. Biol.* 63:1-38; Soderling and Beavo, *Curr. Opin. Cell Biol.* 12:174-179, 2000; and Francis et al., *Prog. Nucleic Acid Res. Mol. Biol.* 65:1-52, 2001). Some of the 11 families include more than one member, with each member of the sub-family being identified by a capital letter after the Arabic number identifying the family (e.g., PDE4A, PDE4B, PDE4C, and PDE4D). Even further, most of the genes encoding PDEs have more than one promoter and the coding sequence is alternatively spliced. The splice variants are designated by a further Arabic numeral following the sub-family designation. For example, PDE4D3 is a PDE within family 4, sub-family D, and is designated as the third splice variant. There are at least 100 different PDE open reading frames (Halpin, supra, referencing Conti and Beavo, *Annu. Rev. Biochem.* 76:481-511, 2007).

Phosphodiesterase 4B (PDE4B) plays a key role in regulating inflammation. Roflumilast, a PDE4-selective inhibitor, has recently been approved for treating severe chronic obstructive pulmonary disease (COPD) patients with exacerbation. However, there is also clinical evidence suggesting the development of tachyphylaxis or tolerance on repeated dosing of roflumilast. Accordingly, there is a need for an improved therapy that would ameliorate the development of tolerance against roflumilast.

SUMMARY

In a first aspect, the present invention features pharmaceutical compositions including two active agents; a first agent that inhibits a phosphodiesterase in Family 4 (PDE4; e.g., a compound conforming to Formula I, such as roflumilast) and a second active agent that inhibits the expression or activity of a PDE4 in Family B (PDE4B; e.g., PDE4B2). The second active agent can inhibit the expression or activity of the PDE4B (e.g., PDE4B2) directly or indirectly. For example, a direct inhibitor may inhibit the expression of the gene encoding PDE4B or directly bind to or otherwise directly interact with a PDE4B (e.g., PDE4B2); an indirect inhibitor may inhibit the expression or activity of a molecule other than a PDE4B (e.g., PDE4B2) within the same biochemical pathway. For example, where the compositions include a second active agent that indirectly inhibits the expression or activity of a PDE4B (e.g., PDE4B2), that agent may inhibit the expression of IKKIβ, IκBα, p50, NFκB p65, or PKA-Cβ or the activity of the expressed proteins (e.g., one could inhibit the formation of a complex including p50 and p65 (e.g., the IκBα-p50-p65 complex or the p50-p65-PKA-Cβ complex shown in FIG. 1).

The first and second agents can be, independently, chemical compounds or biological compounds (e.g., a nucleic acid, peptide nucleic acid (PNA), or polypeptide). For example, in one embodiment, the first agent is a chemical compound and the second agent is a nucleic acid; in another embodiment, both the first and second agents are chemical compounds. For example, the present compositions can include a compound of Formula I (e.g., roflumilast) as the first agent and an alkenyldiarylmethane (ADAM) compound (e.g., ADAMS or ADAM6), a derivative thereof, or salt thereof that inhibits the activity of a PDE4B (e.g., PDE4B2). In referring to chemical compounds, and for ease of reading, we may not explicitly refer to derivatives and salts thereof on every occasion. It is to be understood that where a compound described herein is employed, a pharmaceutically active derivative or salt thereof may also be employed. In other embodiments, the second active agent can be a steroid (e.g., a glucocorticoid such as dexamethasone, cortisol, cortisone, prednisone, prednisolone, methylprednisolone, betamethasone, triamcinolone, beclometasone, fludrocortisone acetate, deoxycorticosterone acetate (DOCA) and aldosterone). In some embodiments, the second active agent is dexamethasone, curcumin, or HIF-1α inhibitor.

As described further below, the pharmaceutical compositions can be formulated in various ways for administration to a patient or for use in the preparation of a medicament (e.g., a medicament for inflammation, such as an inflammatory lung disease, or for any other disease, disorder, or condition described herein as amenable to treatment). For example, the present compositions can be formulated as particles for administration by inhalation, as a cream, gel, or ointment for topical administration, as a tablet or capsule for oral administration, or as a solution or suspension for injection (e.g., intravenous, intramuscular, intraperitoneal, or subcutaneous injection). When in unit dosage form, the pharmaceutical compositions can include less of the first agent than would otherwise be required to achieve a certain outcome if the first agent were administered in the absence of the second agent. For example, where the first agent is a compound conforming to Formula I, the amount of that compound administered in the presence of a second agent to achieve a given clinical result can be less than the amount of that compound administered in the absence of the second to achieve substantially the same result. In one embodiment, the first agent is a compound of Formula I (e.g., roflumilast) that is present in a unit dosage form in the amount of about 500 mcg. As used herein, the term "about" means±10% of a referenced value (e.g., about 500 mcg of roflumilast is 450-550 mcg of roflumilast) or a value that includes an inherent variation of error for the device or the method being employed to determine the value, whichever is greater. While we may describe the methods herein as methods of treatment, any such descriptions can be equally well presented as "uses" and the invention can be claimed as the use of a composition described herein in, for example, the preparation of a medicament or in the preparation of a medicament for treating a disease, disorder or condition described herein (in accordance with varying patent practices throughout the world).

As noted, the first and second active agents can be nucleic acid molecules that selectively inhibit the expression of a PDE4 (e.g., a PDE in the 4A or 4B subfamilies) or, in the case of the second agent, selectively inhibit a PDE4B (e.g., PDE4B2).

In another aspect, the invention features kits including the compositions described herein. Within the kits, the first and second agents (or pluralities thereof) can be combined or contained separately, together with instructions for use. In one embodiment, the invention features a kit comprising roflumilast, a second active agent that inhibits the expression or activity of a PDE4B (e.g., PDE4B2), instructions for use, and, optionally, one or more of a diluent, delivery device or dressing for use in administering the first or second active agent to a patient.

In another aspect, the invention features an isolated cell that stably overexpresses a PDE4B (e.g., PDE4B2). The cell may be a primary cell or may be immoralized and can be one of an established cell line. The cell can be a human cell. These cells can be used, among other things, in screening assays to identify inhibitors of PDE4/PDE4B/PDE4B2-mediated inflammation. The PDE4/PDE4B/PDE4B2 gene product can be expressed from an expression vector such as a viral vector or plasmid or integrated into the cell's genome. In either event the overexpression can be driven from a constitutively active or inducible promoter (e.g., a promoter activated by transcription factors present in a tissue affected by a disease described herein (e.g., a lung tissue-specific promoter).

In another aspect, the invention features methods of treating a patient who has a condition as described herein (e.g., an inflammatory lung disease such as COPD). The methods can be carried out by administering to the patient a therapeutically effective amount of at least one first agent (e.g., a compound of Formula I, such as roflumilast, or rolipram or cilomilast) and at least one second agent that inhibits the expression or activity of a PDE4B (e.g., PDE4B2). The first and second agents can be combined in a single dosage form or maintained in two dosage forms that are administered concurrently or sequentially by the same or different routes of administration. For example, the first agent can be administered orally, and the second agent can be administered topically (e.g., as eardrops to the ear to treat otitis media) by inhalation (e.g., to directly access the lungs), or by injection (e.g., intravenously). In another embodiment, both the first and second agents are administered by inhalation (e.g., as a dry powder formulation in which the active agents are associated with a nanoparticle such as a liposome). Accordingly, the invention encompasses dry powder formulations of the first and second agents as well as dry powder and other formulations (e.g., liquids for infusion) in which one or more of the active agents are associated with a nanoparticle, such as a liposome.

In another aspect, the invention features methods of identifying an inhibitor of PDE4B (e.g., PDE4B2). As described further below, we hypothesize that PDE4B2 regulates the expression of pro-inflammatory chemokines, including chemokine (C-C motif) ligand 5 (CCL5), chemokine (C-C motif) ligand 7 (CCL7), C-X-C motif chemokine 10 (CXCL10), and C-X-C motif chemokine 11 (CXCL11) (with CCL5, CCL7, CXCL10, and CXCL11 being referred to as the Group A chemokines), at least in part in a manner that is independent from PDE4B2's well known enzymatic activity. The assay can be variously configured in cultured cells or in vitro and identifies potential PDE4B2 inhibitors by their ability to suppress IKKβ-CA-induced NF-κB promoter activity and Group A chemokine expression in cells transfected with wild type PDE4B2 or an enzymatically crippled PDE4B2 (e.g., the mutant PDE4B2-D392A). The methods can include the steps of providing cells (e.g., cells such as BEAS-2B cells) transfected with an NF-κB reporter vector (e.g., a vector including a detectable tag or detection system such as a luciferase-based system). The cells can optionally express or overexpress (e.g., by way of transfection) IKKβ-CA and a wild type and/or mutant PDE4B2. After a given period of time (e.g., 1-24 hours), NF-κB activity can be measured and the cells can be exposed to a potential inhibitor (e.g., cells in culture can be exposed to an inhibitor for about 1-12 hours) before measuring the expression or activity of NF-κB or a Group A chemokine. A potential inhibitor that suppresses the expression or activity of NF-κB or one or more of the Group A chemokines can be tested further as an inhibitor of PDE4B2.

BRIEF DESCRIPTION OF THE DRAWINGS

In FIGS. 2A-2F, PDE4B mRNA expression was analyzed. FIG. 2A is a bar graph illustrating PDE4B mRNA expression in BEAS-2B cells pretreated with roflumilast (Rof; 0.1 µM) for 1 h followed by a 1.5-hour stimulation with NTHi (MOI of 25, 50, and 100). At each multiplicity of infection, PDE4B mRNA was increased in the Rof-treated, NTHi-stimulated cells relative to control. In FIG. 2B, BEAS-2B cells were pretreated with Rof (0.01, 0.1, and 1 µM) for 1 h followed by a 1.5-hour stimulation with NTHi. At each concentration of Rof, PDE4B mRNA was increased in the Rof-treated, NTHi-stimulated cells relative to control. In FIG. 2C, primary NHBE cells were pretreated with Rof (0.1 µM) for 1 hour followed by a 1.5-hour stimulation with NTHi, increasing PDE4B mRNA significantly relative to control cells. In FIG. 2D, BEAS-2B cells were pretreated with the transcriptional inhibitor actinomycin D (ActD; 5 ng/ml) and Rof (0.1 µM) for 1 hour followed by a 1.5-hour stimulation with NTHi. ActD completely abrogated the PDE4B induction by NTHi and roflumilast, suggesting that the synergistic induction of PDE4B occurs at the transcriptional level (FIG. 2D). In FIG. 2E, mice were inoculated with Rof (5 mg/kg i.p.) for 2 hours, followed by intratracheal inoculation with NTHi ($5\times10^7$ cfu per lung). After 5 hours, PDE4B mRNA expression in lung tissues was analyzed and found to be significantly elevated in Rof-treated, NTHi-stimulated cells. In FIG. 2F, BEAS-2B cells were pretreated with Rof (0.1 µM) for 1 hour followed by a 1.5-hour stimulation with NTHi or TNF-α (10 ng/mL). In FIG. 2G, BEAS-2B cells were pretreated with Rof (0.1 µM) for 1 hour followed by a 3-hour stimulation with NTHi, and PDE4B2 protein expression was analyzed. In FIGS. 2H and 2I, mice were inoculated with Rof and NTHi as described in E. After 5 hours, PDE4B2 protein expression in lung tissues was analyzed (H) and lung tissues were stained against PDE4B (I). Magnification 200×, scale bar 100 µm. The relative density of PDE4B2 protein was normalized with α-tubulin (G) or β-actin (H). Data in A-E, G, and H are mean±SD (n=3); *P<0.05; n.s.=P>0.05. Data are representative of three or more independent experiments. CON, control; n.s., nonsignificant.

FIG. 3 is a bar graph illustrating that PDE4B siRNA markedly depleted PDE4B2 expression in BEAS-2B cells; see Example 2; PDE4B is required for NTHi-induced expression of proinflammatory mediators.

FIGS. 4A-4B show that increased expression of PDE4B2 enhances NTHi-induced expression of chemokines. FIG. 4A is a photograph of a Western blot showing PDE4B2 expression in mock-transfected cells and cells that stably express PDE4B2. FIG. 4B is a panel of bar graphs illustrating the increased expression of the cytokines CCLS, CCL7, CXCL10, and CXCL11 in the mock- and PDE4B2-transfected cells treated as indicated with NTHi and Rof. The cells were pretreated with Rof for 1 hour followed by a five-hour stimulation with NTHi before mRNA expression was analyzed. The data in FIG. 4B are mean±SD (n=3); *P<0.05.

FIG. 5 is a photograph of a Western blot; protein expression was analyzed after a 48-hour transfection with siRNAs directed to PKA-Cα and PKA-Cβ in BEAS-2B cells. β-actin was analyzed as a control.

FIG. 6 is a cartoon illustrating a drug and an siRNA, either of which may serve as a first or second agent as described herein, associated with a lipid-based nanoparticle for administration to a patient.

FIGS. 7A-7H are a collection of data generated primarily from studies aimed at determining whether dexamethasone can suppress the induction of PDE4B by NTHi and Rof.

FIG. 9 is a representation of the nucleic acid sequence of a human PDE4B2 (SEQ ID NO:2).

FIGS. 10A and 10B are schematic representations of the domains present in PDEs in the eleven known PDE families (A; from Halpin, supra, and originally published by Conti and Beavo, *Annu. Rev. Biochem.* 76:481-511, 2007) and a comparison of the splice variants in PDE4 family (B).

DETAILED DESCRIPTION

Figure 1:
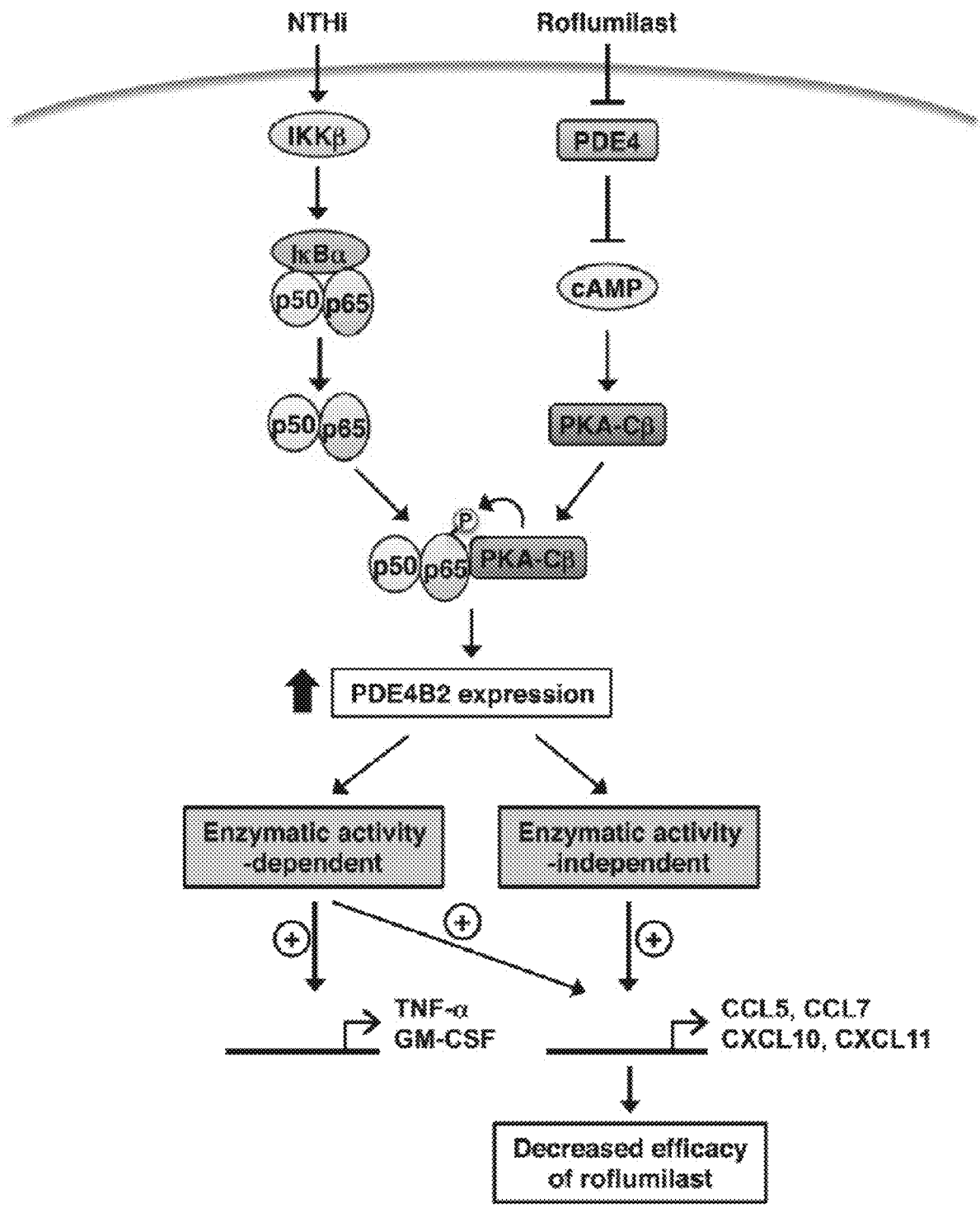
FIG. 1 is a schematic representation of PDE4B2 induction by NTHi and roflumilast via p65 and PKA-β.

The compositions of the present invention include formulations (e.g., pharmaceutical or physiologically acceptable formulations) that can include two or more active agents that are useful in the treatment of inflammation (e.g., an inflammatory lung disease, such as COPD). It will be understood in the art that a pharmaceutical composition/formulation is a non-naturally occurring composition including at least one active agent, and such compositions are considered physiologically acceptable in the sense that they are non-toxic at the dosages prescribed. While the compositions of the invention are not limited to those that achieve a desired outcome by way of any particular mechanism of action, the compositions can include a first agent that inhibits the expression or activity of a PDE4 family member and a second agent that inhibits the expression or activity of one or more of the PDEs in the "B family" (i.e., a PDE4B, such as PDE4B2). In case of doubt, the terms "first agent" and "second agent" are used to indicate that the two agents are different from one another. Further, while selectivity may be preferred, each of the first and second agents may inhibit more than one PDE4 family member and may inhibit one or more of the same PDE4 family members. For example, both the first and second agents may inhibit a phosphodiesterase in family 4, sub-family B, and both the first and second agents may inhibit more than one of the splice variants within a sub-family. For example, both the first and second agents may inhibit PDE4B1 and PDE4B2. In some embodiments, the first and/or second agent inhibits a phosphodiesterase in family 4, sub-family B, to the exclusion of PDEs in other families or subfamilies. For example, the first and/or second agent may inhibit one or more of the splice variants of PDE4B but not any of the splice variants of PDE4D.

We use the terms "active" and "pharmaceutically active" to refer to the ability of an agent to affect its target (e.g. to activate, inhibit, up-regulate, or down-regulate) in vivo. To be "active," the effect an agent has on its target must be sufficient to confer a clinical benefit to a specific patient or generally to a population of patients (recognizing that a response can vary from person-to-person and may not be effective in some individuals).

We use the terms "inhibitor," "inhibiting," "inhibit," and the like to refer to the ability of an agent to reduce the expression or activity of a stated target (here, typically an enzyme in the PDE4 family). While the inhibition does not have to achieve a complete and total reduction in the target's expression or activity, the reduction must occur to such an extent that it confers a benefit to a specific patient or generally to a population of patients (recognizing that a response can vary from person-to-person and may not be effective in some individuals). In the present case, that benefit can be, for example, an improved reaction to treatment with a PDE4 inhibitor such as roflumilast, cilomilast, or another PDE4 inhibitor disclosed herein. As noted elsewhere herein, the inhibitor may exert its action on the target directly (e.g., by inhibiting the transcription, translation, or activity of the target itself) or indirectly (e.g., by inhibiting a moiety that acts in a cellular pathway either upstream or downstream from the target). The first agent and the second agent can be, independently, a chemical compound (e.g., a carbon-based small molecule having a molecular mass less than about 1,000 g/mol; a chemical compound may be referred to herein as a "drug"), a nucleic acid (e.g., a nucleic acid that mediates RNAi, a microRNA, or an antisense oligonucleotide), or a polypeptide (e.g., an antibody).

In various embodiments, the compositions and methods can include more than one type of first agent and more than one type of second agent.

The First Agent: In some embodiments, the first agent can be a PDE4 inhibitor. The first agent can be an inhibitor of one or more of PDE4 isoforms, including, PDE4A (e.g., PDE4A1, PDE4A5, PDE4A8, PDE4A10, PDE4A11, and PDE4A7), PDE4B (e.g., PDE4B1, PDE4B2, PDE4B3, and PDE4B4), PDE4C (e.g., PDE4C1), and PDE4D (e.g., PDE4D1, PDE4D2, PDE4D3, PDE4D4, PDE4D5, PDE4D6, PDE4D7, PDE4D8, and PDE4D9).

In one embodiment, the first agent can conform to Formula I

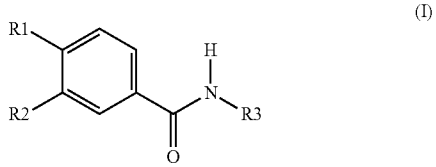

(I)

as described in U.S. Pat. No. 5,712,298, the entire content of which is incorporated herein by the present reference thereto. With regard to Formula I, one of the substituents R1 and R2 is hydrogen, 1-6C-alkoxy, 3-7C-cycloalkoxy, 3-7C-cycloalkylmethoxy, benzyloxy or 1-4C-alkoxy that is completely or partially substituted by fluorine, and the other is 1-4C-alkoxy that is completely or partially substituted by fluorine;

R3 is phenyl, pyridyl, phenyl that is substituted by R31, R32 and R33 or pyridyl that is substituted by R34, R35, R36 and R37, where R31 is hydroxyl, halogen, cyano, carboxyl, trifluoromethyl, 1-4C-alkyl, 1-4C-alkoxy, 1-4C-alkoxycarbonyl, 1-4C-alkylcarbonyl, 1-4C-alkylcarbonyloxy, amino, mono- or di-1-4C-alkylamino or 1-4C-alkylcarbonylamino;

R32 is hydrogen, hydroxyl, halogen, amino, trifluoromethyl, 1-4C-alkyl or 1-4C-alkoxy;

R33 is hydrogen, halogen, 1-4C-alkyl or 1-4C-alkoxy;

R34 is hydroxyl; halogen, cyano, carboxyl, alkyl, 1-4C-alkoxy, 1-4C-alkoxycarbonyl or amino;

R35 is hydrogen, halogen, amino or 1-4C-alkyl;

R36 is hydrogen or halogen; and

R37 is hydrogen or halogen, the salts of these compounds, and the N-oxides of the pyridines and their salts.

In certain embodiments, R1 is 1-4C-alkoxy that is completely or partially substituted by fluorine.

In other embodiments, R1 is methoxy which is completely or partially substituted by fluorine.

In a particular embodiment, R1 is difluoromethoxy.

In certain embodiments, R2 is 3-5C-cycloalkoxy or 3-5C-cycloalkylmethoxy.

In another embodiment, R2 is 3-5C-cycloalkylmethoxy.

In a particular embodiment, R2 is cyclopropylmethoxy.

In certain embodiments, R3 is pyridyl, or pyridyl that is substituted by R34, R35, R36 and R37.

In other embodiments, R3 is pyridyl that is substituted by R34, R35, R36 and R37.

In a particular embodiment, R3 is 3,5-dichloropyrid-4-yl.

In certain embodiments, R1 is 1-4C-alkoxy that is completely or partially substituted by fluorine; R2 is 3-5C-cycloalkoxy or 3-5C-cycloalkylmethoxy; and R3 is pyridyl, or pyridyl that is substituted by R34, R35, R36 and R37.

In other embodiments, R1 is methoxy which is completely or partially substituted by fluorine; R2 is 3-5C-cycloalkylmethoxy; and R3 is pyridyl that is substituted by R34, R35, R36 and R37.

In certain particular embodiments, R34 is halogen or 1-4C-alkyl; R35 is hydrogen, halogen; R36 is hydrogen or halogen.

In a particular embodiment, R1 is difluoromethoxy; R2 is cyclopropylmethoxy; and R3 is 3,5-dichloropyrid-4-yl.

1-6C-Alkoxy is a radical which, in addition to the oxygen atom, contains a straight-chain or branched alkyl radical having 1 to 6 carbon atoms. Alkyl radicals having 1 to 6 carbon atoms which may be mentioned in this context are, for example, the hexyl, isohexyl (2-methylpentyl), neohexyl (2,2-dimethylbutyl), pentyl, isopentyl (3-methylbutyl), neopentyl (2,2-dimethylpropyl), butyl, isobutyl, sec-butyl, tert-butyl, propyl, isopropyl, ethyl and methyl radicals.

3-7C-Cycloalkoxy is, for example, cyclopropyloxy, cyclobutyloxy, cyclopentyloxy, cyclohexyloxy and cycloheptyloxy.

3-7C-Cycloalkylmethoxy is, for example, cyclopropylmethoxy, cyclobutylmethoxy, cyclopentylmethoxy, cyclohexylmethoxy and cycloheptylmethoxy.

1-4C-Alkoxy which is completely or partially substituted by fluorine is, for example, the 1,2,2-trifluoroethoxy, the 2,2,3,3,3-pentafluoropropoxy, the perfluoroethoxy and in particular the 1,1,2,2-tetrafluoroethoxy, the trifluoromethoxy, the 2,2,2-trifluoroethoxy and the difluoromethoxy radical.

Halogen within the meaning of the present invention is bromine, chlorine and fluorine.

1-4C-Alkyl is a straight-chain or branched alkyl radical having 1 to 4 carbon atoms. Examples are the butyl, isobutyl, sec-butyl, tert-butyl, propyl, isopropyl, ethyl and methyl radicals 1-4C-Alkoxy is a radical which, an addition to the oxygen atom, contains one of the abovementioned 1-4C-alkyl radicals. Examples are the methoxy and the ethoxy radicals.

1-4C-Alkoxycarbonyl is a carbonyl group to which one of the abovementioned 1-4C-alkoxy radicals is bonded. Examples are the methoxycarbonyl (CH$_3$O—CO—) and the ethoxycarbonyl radical (CH$_3$CH$_2$O—CO—).

1-4C-Alkylcarbonyl is a carbonyl group to which one of the abovementioned 1-4C-alkyl radicals is bonded. An example is the acetyl radical (CH$_3$CO—).

1-4C-Alkylcarbonyloxy radicals contain, in addition to the oxygen atom, one of the abovementioned 1-4C-alkylcarbonyl radicals. An example is the acetoxy radical (CH$_3$CO—O—).

Mono- or di-1-4C-alkylamino radicals are, for example, the methylamino, the dimethylamino and the diethylamino radicals.

A 1-4C-alkylcarbonylamino radical is, for example, the acetamido radical (—NH—CO—CH$_3$).

Exemplary phenyl radicals substituted by R31, R32 and R33 are the radicals 2-acetylphenyl, 2-aminophenyl, 2-bromophenyl, 2-chlorophenyl, 2,3-dichlorophenyl, 2,4-dichlorophenyl, 4-diethylamino-2-methylphenyl, 4-bromo-2-trifluoromethylphenyl, 2-carboxy-5-chlorophenyl, 3,5-dichloro-2-hydroxyphenyl, 2-bromo-4-carboxy-5-hydroxyphenyl, 2,6-dichlorophenyl, 2,5-dichlorophenyl, 2,4,6-trichlorophenyl, 2,4,6-trifluorophenyl, 2,6-dibromophenyl, 2-cyanophenyl, 4-cyano-2-fluorophenyl, 2-fluorophenyl, 2,4-difluorophenyl, 2,6-difluorophenyl, 2-chloro-6-fluorophenyl, 2-hydroxyphenyl, 2-hydroxy-4-methoxyphenyl, 2,4-dihydroxyphenyl, 2-methoxyphenyl, 2,3-dimethoxyphenyl, 2,4-dimethoxyphenyl, 2,6-dimethoxyphenyl, 2-dimethylaminophenyl, 2-methylphenyl, 2-chloro-6-methylphenol, 2,4-dimethylphenyl, 2,6-dimethylphenyl, 2,3-dimethylphenyl, 2-methoxycarbonylphenyl, 2-trifluoromethylphenyl, 2,6-dichloro-4-methoxyphenyl, 2,6-dichloro-4-cyanophenyl, 2,6-dichloro-4-aminophenyl, 2,6-dichloro-4-methoxycarbonylphenyl, 4-acetylamino-2,6-dichlorophenyl and 2,6-dichloro-4-ethoxycarbonylphenyl.

Exemplary pyridyl radicals substituted by R34, R35, R36 and R37 are the radicals 3,5-dichloropyrid-4-yl, 2,6-diaminopyrid-3-yl, 4-aminopyrid-3-yl, 3-methylpyrid-2-yl, 4-methylpyrid-2-yl, 5-hydroxypyrid-2-yl, 4-chloropyrid-3-yl, 3-chloropyrid-2-yl, 3-chloropyrid-4-yl, 2-chloropyrid-3-yl, 2,3,5,6-tetrafluoropyrid-4-yl, 3,5-dichloro-2,6-difluoropyrid-4-yl, 3,5-dibromopyrid-2-yl, 3,5-dibromopyrid-4-yl, 3,5-dichloropyrid-4-yl, 2,6-dichloropyrid-3-yl, 3,5-dimethylpyrid-4-yl, 3-chloro-2,5,6-trifluoropyrid-4-yl and 2,3,5-trifluoropyrid-4-yl.

Suitable salts of the compounds described herein (e.g., compounds of Formula I), depending on substitution, are all acid addition salts, but in particular all salts with bases. In particular, the salts can be pharmacologically tolerable, inorganic or organic acids and bases customarily used in pharmacy. Pharmacologically intolerable salts, which can be obtained, for example, as process products during the preparation of the compounds on an industrial scale, are converted into pharmacologically tolerable salts by processes known to one of ordinary skill in the art. Suitable salts include water-soluble and water-insoluble acid addition salts with acids, such as, for example, hydrochloric acid, hydrobromic acid, phosphoric acid, nitric acid, sulphuric acid, acetic acid, citric acid, D-gluconic acid, benzoic acid, 2-(4-hydroxybenzoyl)benzoic acid, butyric acid, sulphosalicylic acid, maleic acid, lauric acid, malic acid, fumaric acid, succinic acid, oxalic acid, tartaric acid, embonic acid, stearic acid, toluenesulphonic acid, methanesulphonic acid and 3-hydroxy-2-naphthoic acid, the acids being employed in salt preparation in an equimolar quantitative ratio or one differing therefrom depending on whether a mono- or polybasic acid is concerned and depending on which salt is desired. Other suitable salts are salts with bases. Examples of basic salts are lithium, sodium, potassium, calcium, aluminum, magnesium, titanium, ammonium, meglumine, tromethamine, or guanidinium salts. The bases being employed in basic salt preparation can be present in an equimolar quantitative ratio or one differing therefrom.

In one embodiment, the first agent is roflumilast or a salt thereof:

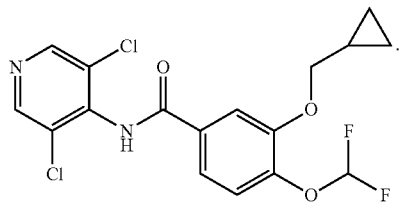 [SMILES: O=C(Nc1c(Cl)cncc1Cl)c1ccc(OC(F)F)c(OCC2CC2)c1]

In one embodiment, the first agent is rolipram or a salt thereof:

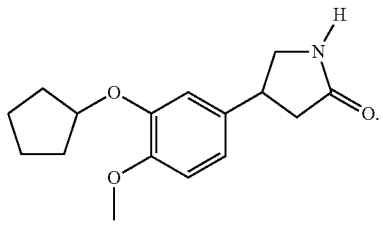 [SMILES: COc1ccc(C2CNC(=O)C2)cc1OC1CCCC1]

Chemical compounds useful in the present compositions and methods can be purchased or synthesized, isolated, or purified by methods known in the art. Other compounds that can be employed as the first agent include cilomilast (developed by GlaxoSmithKline; see Christensen et al., *J. Med. Chem.* 41:821-835, 1998); BAY 19-8004 (developed by Bayer PLC; see Grootendorst et al., *Pulm. Pharmacol. Ther.* 16:341-347, 2003; AWD 12-281 (developed by Elbion AG/GlaxoSmithKline; see Gutke et al., *Curr. Opin. Investig. Drugs* 6:1149-1158, 2005); cipamfylline, FRL-61063 (developed by Leo Pharmaceuticals; see Kucharekova et al., *Arch. Dermatol. Res.* 295:29-32, 2003); mesopram, SH-636 (developed by Schering A G; see Loher et al., *J. Pharmacol. Exp. Ther.* 305:549-556, 2003); CC-10004 (developed by Celgene; see Baumer et al., *Inflamm. Allergy Drug Targets* 6:17-26, 2007); oglemilast, GRC-3886 (developed by Glenmark; see Enefer, *Inflammation 2005—Seventh World Congress. Highlights I. IDrugs,* 8:788-790, 2005), tetomilast, OPC-6535 (developed by Otsuka; see Chihiro et al., *J. Med. Chem.* 38:353-358, 1995); tofimilast, CP-325366 (developed by Pfizer; see Duplantier et al., *J. Med. Chem.* 50:344-349, 2007); ONO-6126 (developed by Ono Pharmaceuticals; see Furuie et al., *Eur. Respir. J.* 22(Suppl 45):395s, 2003); CI-1044 (developed by Pfizer; see Ouagued et al., *Pulm. Pharmacol. Ther.* 18:49-54, 2005); HT-0712 (developed by Inflazyme/Helicon; see MacDonald et al., *Neurorehabil. Neural Repair* 21:486-496, 2007); ibudilast (developed by Merck-Frosst; see Huang et al., *Life. Sci.* 78:2663-2668, 2006); MK-0873 (developed by Merck; see Boot et al., *Pulm. Pharmacol. Ther.* 2008); arofylline, LAS-31025 (developed by Almirall; see Beleta et al., *Third International Conference on Cyclic Nucleotide Phosphodiesterases: From Genes to Therapies,* Glasgow, 1996); CI-1018 (developed by Pfizer; see Burnouf et al., *J. Med. Chem.* 43:4850-4867, 2000); T-2585 (developed by Tanabe; see Ukita et al., *J. Med. Chem.* 42:1088-1099, 1999); YM-976 (developed by Yamanouchi; see Aoki et al., *J. Pharmacol. Exp. Ther.* 295:255-260, 2000); V-11294A (developed by Napp; see Gale et al., *Br. J. Clin. Pharmacol.* 54:478-484, 2002); piclamilast, RP-73401 (developed by Rohne-Poulenc-Rorer; see Chen et al., *Acta Pharmacol. Sin.* 25:1171-1175, 2004); atizoram, CP-80633 (developed by Pfizer; see Wright et al., *Can. J. Physiol. Pharmacol.* 75:1001-1008, 1997); filaminast, WAY-PDA-641 (developed by Wyeth-Ayerst; see Heaslip et al., *J. Pharmacol. Exp. Ther.* 268:888-896, 1994); SCH 351591 (developed by Schering-Plough; see Billah et al., *J. Pharmacol. Exp. Ther.* 302:127-137, 2002); IC-485 (developed by ICOS Corporation); lirimilast, BAY-19-8004 (developed by Bayer; see Sturton and Fitzgerald, *Chest* 121:192S-196S, 2002), D4418 (developed by Celltech/Schering-Plough; see Buckley et al., *Bioorg. Med. Chem. Lett.* 10:2137-2140, 2000); CDP-840 (developed by Celltech/Merck-Frosst; see Alexander et al., *Bioorg. Med.*

*Chem. Lett.* 12:1451-1456, 2002); L-826,141 (developed by Celltech/Merck-Frosst; see Claveau et al., *J. Pharmacol. Exp. Ther.* 310:752-760, 2004); AN2728 (under development by Anacor Pharmaceuticals); apremilast (developed by Celgene); diazepam (developed by Hoffmann-La Roche 1963); luteolin (supplement extracted from peanuts that also possesses IGF-1 properties); and mesembrenone (an alkaloid from the herb *Sceletium tortuosum*).

In certain embodiments, the first agent can up-regulate the expression or increase the activity of one or more PDE4 isoforms, including PDE4B isoforms, either by itself or in concert with other factors in the biological environment. The PDE4B isoform can be PDE4B1, PDE4B2, PDE4B3, or PDE4B4, and the factors in the biological environment can include one or more of cyclic adenosine monophosphate (cAMP) elevators, lipopolysaccharide (LPE), or bacteria. The bacteria can be nontypeable *Haemophilus influenzae* (NTHi).

The Second Agent: Any of the first agents described herein can be formulated with, packaged with, or administered with one or more of a second agent that inhibits, directly or indirectly, the expression or activity of a PDE4B (e.g., PDE4B2). In certain embodiments, the second agent can inhibit one or more other PDE4B isoforms, either instead of PDE4B2 or in addition to PDE4B2. As noted above, the second agent can inhibit one or more of the splice Variants of PDE4B but not any of the splice variants of PDE4D.

The second agent can inhibit one or more of the genes and/or enzymes that can up-regulate expression of a PDE4B isoform (e.g., PDE4B2). For example, the second agent may inhibit the expression of IκB kinase β (IKKβ), IκBα, transcription factor nuclear factor-kβ (NFκB) or a subunit thereof (e.g., p50 or p65), or protein kinase A-Cβ (PKA-Cβ) or the activity of the expressed proteins (e.g., one could inhibit the formation of a complex including p50 and p65 (e.g., the IκBα-p50-p65 complex or the p50-p65-PKA-Cβ complex shown in FIG. 1)

The second agent can inhibit one or more of the cellular pathways that PDE4B (e.g., PDE4B2) may up-regulate. The pathway can be functioning in an enzymatic activity-dependent manner or an enzymatic activity-independent manner.

The second agent can be a glucocorticoid, for example, dexamethasone or a biologically active derivative thereof:

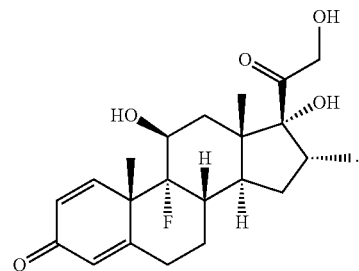

Other useful glucocorticoids include cortisol, cortisone, prednisone, prednisolone, methylprednisolone, betamethasone, triamcinolone, beclometasone, fludrocortisone acetate, deoxycorticosterone acetate (DOCA), aldosterone, budesonide, hydrocortisone, triamcinolone, and pharmaceutically acceptable salts thereof.

The second agent can also be an HIF-la inhibitor. For example, the second agent can be hypoxia inducible factor-1α inhibitor, dimethyloxaloylglycine (DMOG), chrysin, chetomin, YC-1, dimethyl-bisphenol A, 2-methoxyestradiol, IOX2, BAY 87-2243, PX-478 2HCI, FG-2261, KC7F2, cryptotanshinone, EF-24, FM19G11, or PX 12. In certain embodiments, the second agent can be 17-dimethylamino-ethylamino-17-demethoxygeldanamycin (17-DMAG) or a derivative or salt thereof:

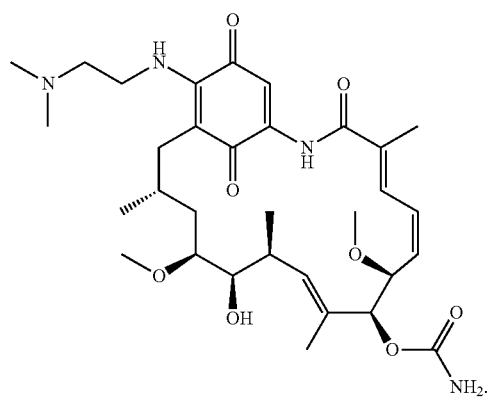 [SMILES: CO[C@H]1/C=C\C=C(/C)C(=O)NC2=CC(=O)C(NCCN(C)C)=C(C[C@@H](C)C[C@H](OC)[C@H](O)[C@@H](C)/C=C(\C)[C@@H]1OC(N)=O)C2=O]

The second agent can also be curcumin (i.e., (1E,6E)-1,7-Bis(4-hydroxy-3-methoxyphenyl)-1,6-heptadiene-3,5-dione) or a derivative or salt thereof:

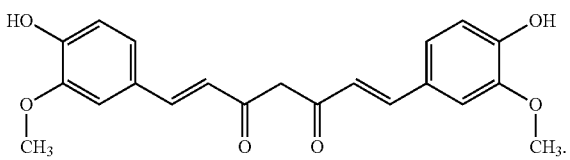 [SMILES: COc1cc(/C=C/C(=O)CC(=O)/C=C/c2ccc(O)c(OC)c2)ccc1O]

The second agent can be or include ADAMS or ADAM6 (Cullen et al., *Bioorg. Med. Chem. Lett.* 18:1530-1533, 2008) or a pharmaceutically active derivative or salt thereof:

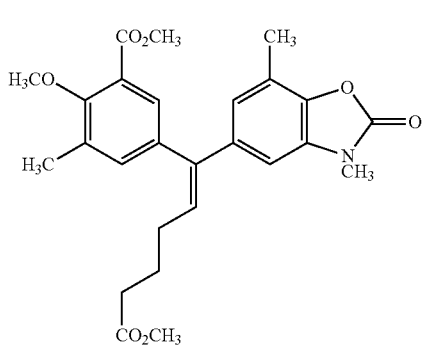

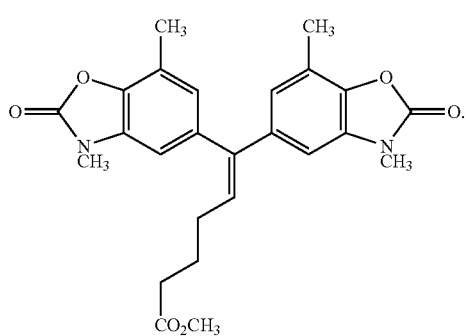

The second agent can also be or include compound A-33 developed from a lead 2-arylpyrimidine derivative as described by Naganuma et al. (*Bioorganic & Medicinal Chemistry Letters* 19(12):3174-3176, 2009), including compound 33 or a pharmaceutically active derivative or salt thereof:

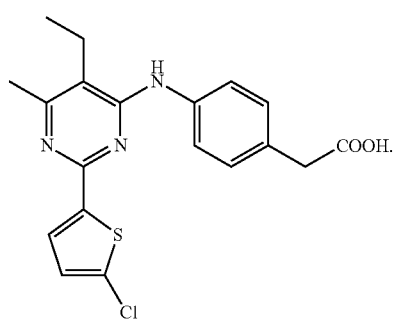

PDE4B IC$_{50}$ = 15 nM
PDE4D IC$_{50}$ = 1700 nM

Triazine derivatives are also known to be potent inhibitors of PDE4B and can be used as second agents in the various embodiments of the present invention (Hagen et al., *Bioorg. Med. Chem. Lett.* 24(16):4031-4034, 2014). Structural studies known in the art have demonstrated that potent and selective PDE4B inhibitors can bind CR3 (Control Region 3, located on the carboxyl side of the catalytic domain) and thereby lock the enzyme in a closed conformation. PDE4B selectivity is believed to be due to a single amino acid polymorphism in CR3 that selects the helical registration of the domain when it closes over the active site. Exchange of a leucine in PDE4B CR3 for a glutamine in PDE4D causes a 70-80 fold shift in inhibitor selectivity. After noting the foregoing, Hagen et al. (supra) describe a series of triazine analogs that similarly bind to CR3 thereby resulting in PDE4B specificity (Hagen et al., supra).

The second agent can conform to Formula II:

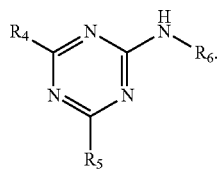

With regard to Formula II, each of R4, R5, and R6 is hydrogen, halogen, cyano, carboxyl, alkyl, aryl, or heterocycle and can be optionally substituted with one or more halogen, cyano, carboxyl, alkyl (e.g., methyl, ethyl, propyl, isopropyl, cyclopropyl), aryl, or heterocycle.

In certain embodiments, R4 can be methyl, ethyl, propyl, isopropyl, or cyclopropyl. R5 can be aryl that is optionally substituted with halogen (e.g., F or Cl) or heterocycle (e.g., furan or thiofuran) that is optionally substituted with halogen (e.g., F or Cl). R6 can be aryl that is optionally substituted with carboxylic acid, alkyl carboxylic acid (e.g., $CH_2CO_2H$, $CH_2(CH_3)CO_2H$, $CH_2(CH_3)_2CO_2H$), halogen (e.g., F or Cl), heterocycle (e.g., piperidinone, imidazolidinone, tetrazole), cyano, alkyl cyano (e.g., $CH_2CN$), alkyl heterocycle, sulfonamide, or aminosulfonamide, or a derivative thereof.

Other compounds useful as second agents include substituted pyridazino[4,5-b]indolizines as described by Donnell et al. (*Bioorganic & Medicinal Chemistry Letters* 20(7): 2163-2167, 2010). For example, one can employ the compound:

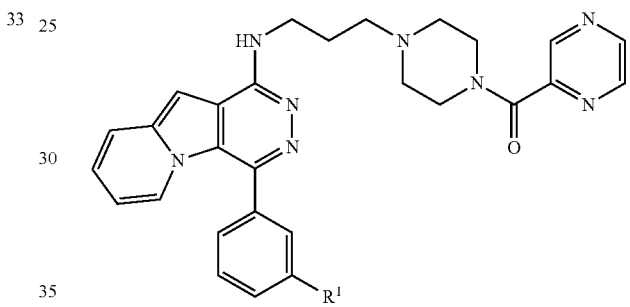

Figure 8A:
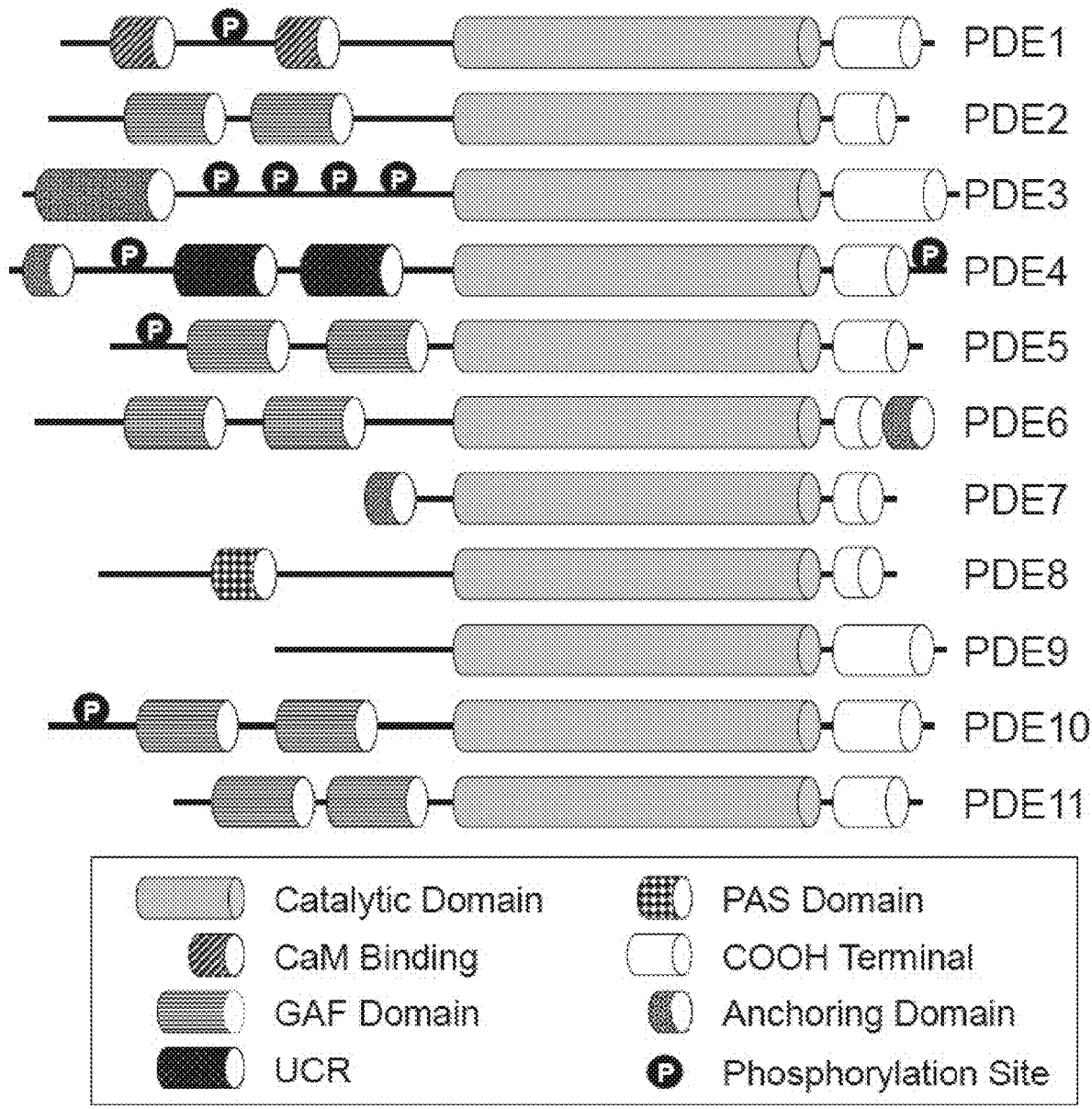
FIG. 8 is a representation of the mRNA sequence of human PDE4B (SEQ ID NO:1).
Figure 8B:
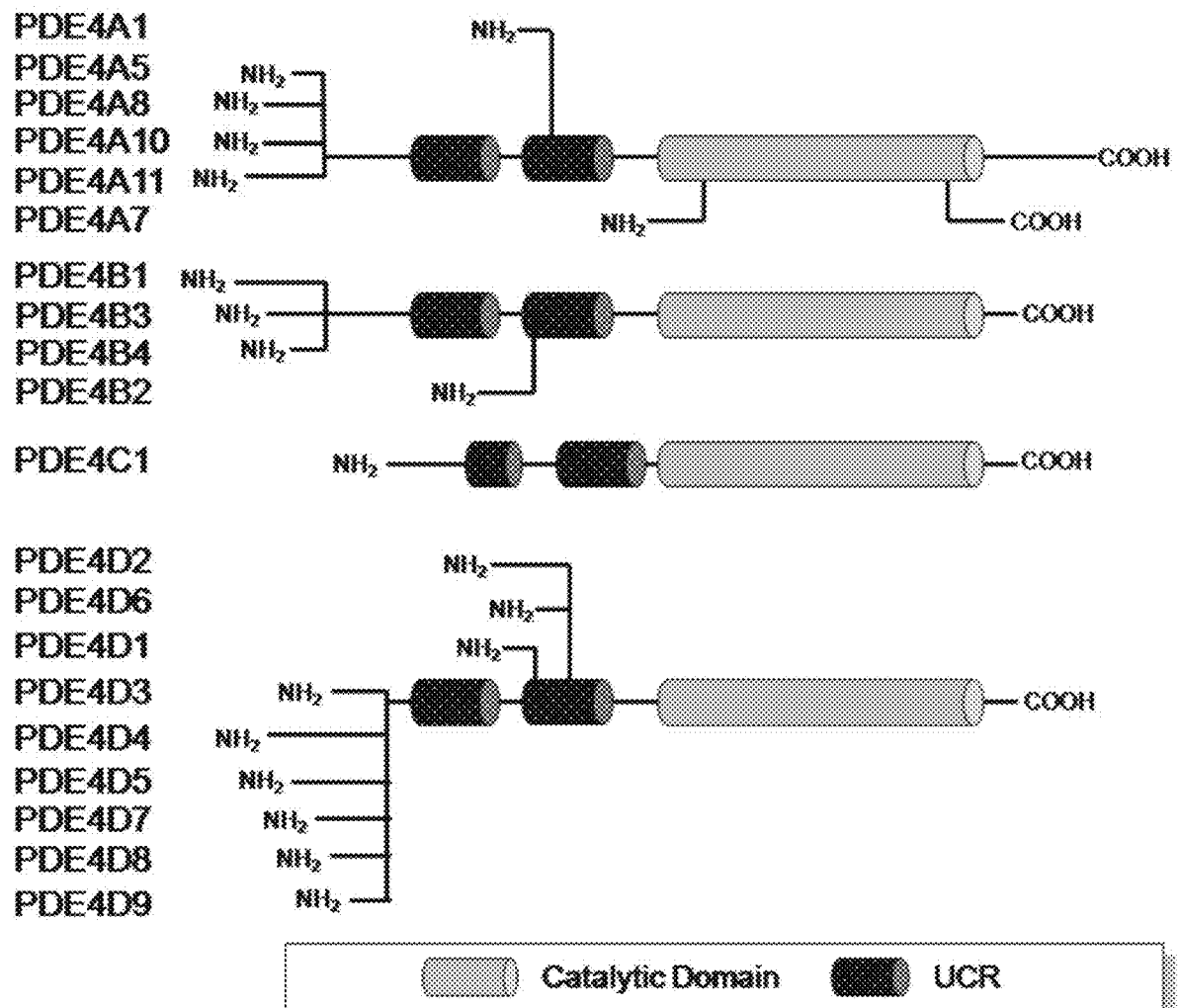

15, R = H, PDE4B K$_i$ = 41 nM
16, R = NO$_2$ PDE4B K$_i$ = 5.6 nM or a pharmaceutically active derivative or salt thereof.

Where the second agent is a nucleic acid, it can be a nucleic acid that mediates RNAi (e.g., an siRNA or shRNA) by targeting and inhibiting the expression of PDE4B2 or another target described herein, such as PKA-Cβ. Other useful nucleic acid-based inhibitors include microRNAs and antisense oligonucleotides. Relevant sequences and methods for generating inhibitory RNA molecules are known in the art. For easy reference, the mRNA sequence of human PDE4B is shown in FIG. 8. Information regarding a 1.6 kb partial PDE4B cDNA, including primers useful in the generation of various PDE4B isoforms and sequence comparisons can be found, as needed, in a report of the cloning of human PDE4B3 (Huston et al., *Biochem. J.*, 328:549-558, 1997; see also Bolger et al., *Mol. Cell. Biol.*, 136558-6571, 1993; McLaughlin et al., *J. Biol. Chem.*, 268:6470-6476, 1993; and Obernolte et al., *Gene*, 129:239-247, 1993). In targeting PDE4B2, the selected agent (e.g., an siRNA that inhibits PDE4B2) may do so selectively (i.e., the agent may inhibit the expression of only PDE4B2 to the exclusion of other PDE4B variants or other PDE4 family members) or non-selectively (i.e., the agent may inhibit PDE4B2 as well as other PDE4B variants or other PDE4 family members). The mRNA sequence of PKA-Cβ is available through, for example, the NCBI "GenBank" website (see, e.g., Accession No. NM-002731 and Taylor et al., *Annu. Rev. Biochem.*, 59:971-1005, 1990).

It has been shown in the art that highly selective PDE4B inhibitors can be designed by exploiting sequence differences outside the active site (see Fox et al., *Cellular Signalling* 26:657-663, 2014). Specifically, PDE4B selectivity can be achieved by capture of a C-terminal regulatory helix termed CR3 (Control Region 3), across the active site in a conformation that closes access by cAMP.

The mRNA sequence of PKA-Cβ is available through, for example, the NCBI "GenBank" website (see, e.g., Accession No. NM-002731 and Taylor et al., *Annu. Rev. Biochem.*, 59:971-1005, 1990).

The second agent can be a siRNA or a fragment thereof. siRNAs useful as the second agent (i.e., as an agent that inhibits, directly or indirectly, the expression or activity of PDE4B2) are commercially available from, for example, Santa Cruz Biotechnology, Inc. (current catalog #sc-41599) and GE HealthCare. siRNAs, shRNAs, microRNAs and antisense oligonucleotides, frequently 19-21 nucleotides in length, can be synthesized according to methods known in the art and customized as desired based on the sequence of the target to be inhibited. Where the second agent is an inhibitory RNA, all of the agents may have a single sequence or may be a pool of different sequences (e.g., a pool of 3-7 siRNAs that inhibit the expression of PDE4B2, PKA-Cβ, or another target described herein).

The second agent can be a polypeptides or a fragment thereof. Polypeptides useful as the first or second agent include antibodies that specifically bind a target as described herein and, where the target is PKA-Cβ, the polypeptide can be TTYADFIASGRTGRRNAIHD (SEQ ID NO:3) or an active fragment or other variant thereof.

As described in the Examples below, an IKKβ inhibitor significantly inhibited the synergistic induction of PDE4B2 by NTHi and roflumilast, but did not affect the induction of PDE4B2 by roflumilast alone. Therefore, in patients where COPD is exacerbated by or associated with NTHi infection, treatment can be carried out with, for example, roflumilast and an IKKβ inhibitor.

Formulations: In various embodiments, the first agent and the second agent can be formulated to be administrated simultaneously or separately. The first agent and/or the second agent can be formulated in the form of a pill, a capsule, a granule, a tablet, a pallet, a suspension, an injection, an infusion, a suppository, a continuous delivery system, a syrup, a tincture, an ointment, a cream, eye drops, ear drops, a flush, a lavage, a slow absorbing depot, a dressing, a lozenge, or any pharmaceutically acceptable application or as a nutritional supplement.

The first agent and/or the second agent, as disclosed herein, can be administered by any route appropriate to the condition to be treated. Suitable routes can include oral, inhalation, parenteral (including subcutaneous, intramuscular, intravenous, intradermal, intrathecal and epidural), rectal, nasal, topical, vaginal, and the like.

When used for oral administration, the formulations can be tablets, troches, lozenges, aqueous or oil suspensions, dispersible powders or granules, emulsions, hard or soft capsules, syrups or elixirs.

When used for inhalation administration, the formulations can include aerosol or dry powder including small particles. The formulation can also be a suspension (e.g., the first and/or second agent particles suspended in the liquefied propellant) or a solution (e.g., the first and/or second agents dissolved in liquefied propellant. The particles can be in sizes of about 10 µm or less. Preferably, the particles can be in sizes less than 5 µm (e.g., 2-3 µm). The formulations can be prepared according to conventional methods and may be delivered with other therapeutic agents. The formulation can further include one or more of HFA propellant, surfactant co-solvent and/or excipient.

When used for parenteral administration, formulation can include aqueous and nonaqueous sterile injection solutions which can contain anti-oxidants, buffers, bacteriostats and solutes which render the formulation isotonic with the blood of the intended recipient; and aqueous and non-aqueous sterile suspensions which can include suspending agents and thickening agents. When used for injection, the pharmaceutical compositions of the first agent and/or the second agent can be in the form of a sterile injectable preparation (e.g., a sterile injectable aqueous or oleaginous suspension). The sterile injectable preparation can also be a sterile injectable solution or suspension in a non-toxic parenterally acceptable diluent or solvent (e.g., a solution in 1,3-butane-diol or prepared as a lyophilized powder).

Kits: The kits of the invention can include any one or more of the compositions described herein, including pharmaceutical compositions containing the first and second agents described herein in a formulation that is ready to administer or can be administered after further manipulation (e.g., after dilution or resuspension). In some embodiments, the first agent and the second agent are within separate containers and packaged together within the kit. In any embodiment, the kit can include instructions for use (e.g., a written document, a disclosure of a web address, or an audio or visual presentation). In any embodiment, the kit can include paraphernalia useful in administering the compositions contained therein (e.g., a needle, syringe, tubing, sterilant, gloves, mask, nebulizer, dropper, gauze, tape, or dressing). The kit can include one or more inhalation devices, for examples, an atomizer, nebulizer, vaporizer, metered dose inhaler (MDI), dry powdered inhaler, or the like.

Conditions amenable to treatment: The compositions of the invention can be employed in human and veterinary medicine as therapeutics, where they can be used, for example, for the treatment and prophylaxis of the following illnesses: acute and chronic (in particular inflammatory and allergen-induced) airway disorders of varying origin (bronchitis, allergic bronchitis, bronchial asthma); dermatoses (especially of proliferative, inflammatory and allergic type), such as psoriasis (vulgaris), toxic and allergic contact eczema, atopic eczema, seborrhoeic eczema, Lichen simplex, sunburn, pruritus in the anogenital area, alopecia areata, hypertrophic scars, discoid lupus erythematosus, follicular and widespread pyodermias, endogenous and exogenous ache, acne rosacea and other proliferative, inflammatory and allergic skin disorders; disorders which are based on an excessive release of TNF (e.g., TNFα) and leukotrienes, for example disorders of the arthritis type (rheumatoid arthritis, rheumatoid spondylitis, osteoarthritis and other arthritic conditions and inflammation of the joints), disorders of the immune system (AIDS), types of shock (septic shock, endotoxin shock, gram-negative sepsis, toxic shock syndrome and ARDS (adult respiratory distress syndrome)) and also generalized inflammations in the gastrointestinal region (Crohn's disease and ulcerative colitis); disorders which are based on allergic and/or chronic, immunological false reactions in the region of the upper airways (pharynx, nose) and the adjacent regions (paranasal sinuses, eyes), such as allergic rhinitis/sinusitis, chronic rhinitis/sinusitis, allergic conjunctivitis and also nasal polyps; otitis media and other ear and sinus infections; but also disorders of the heart which can be treated by PDE inhibitors, such as cardiac insufficiency, or disorders which can be treated on account of the tissue-relaxant action of the PDE inhibitors, such as colics of the kidneys and of the ureters in connection with kidney stones. Inflammation of the eye and tissues surrounding and affecting the eye can also be treated. While the invention is not limited to treatment of conditions that arise due to any particular molecular mechanism, treatable conditions may be recognized as associated with misexpression (e.g., overexpression) of histamine, platelet-activating factor (PAF), arachidonic acid derivatives such as leukotrienes and prostaglandins, cytokines, such as any of IL-1 to IL-12, alpha-, beta-, or gamma-interferon, tumor necrosis factor (TNF), or oxygen free radicals and proteases. In conditions affecting the respiratory system (including any part of the respiratory tract from the nose to the alveoli), ears, or sinuses, the condition to be treated may be one in which mucus is overproduced.

Embodiments in which the first agent is Roflumilast: Roflumilast is useful in the treatment of inflammatory conditions of the lungs (e.g., chronic obstructive pulmonary disease (COPD), COPD associated with chronic bronchitis, and COPD exacerbations). *Haemophilus influenzae* (NTHi), is a major bacterial cause of COPD exacerbation. Accordingly, the present compositions and methods can include roflumilast to reduce the risk of COPD exacerbations in patients with severe COPD associated with chronic bronchitis, a history of exacerbations, and infection with NTHi. Treatment may be contraindicated in patients with moderate to severe liver impairment (Child-Pugh B or C).

The combination therapies described herein may improve one or more of the adverse effects reported in connection with roflumilast treatment (e.g., gastrointestinal problems such as abdominal pain, diarrhea, nausea; related signs such as weight loss and loss of appetite; headaches; back pain; influenza; dizziness; insomnia; anxiety, depression, suicidal thoughts or other mood changes; rhinitis and sinusitis; and urinary tract infections).

The currently recommended dosage of roflumilast for patients with COPD is one 500 mcg tablet per day, with or without food. This dosage may be maintained in the present compositions and methods, increased, or lessened (e.g., to 450-499 mcg/day; 400-450 mcg/day; 300-400 mcg/day; or less than 300 mcg/day (e.g., 100-300 mcg/day)). In other embodiments, topical application forms (such as ointments) for the treatment of dermatoses can contain the first and/or the second active agents in a concentration of, for example, 0.1-99%. The dose for administration by inhalation is customarily between 0.01 and 0.5 mg/kg. The customary dose in the case of systemic therapy is between 0.05 and 2 mg per day.

Auxiliary agents can also be included, and the present compositions can be formulated together with one or more solvents, gel formers, ointment bases and other active compound excipients (e.g., antioxidants, dispersants, emulsifiers, preservatives, solubilizers or permeation promoters), or any combination thereof. Suitable inactive ingredients include lactose monohydrate, corn starch, povidone, and magnesium stearate. Suitable pharmaceutical formulations include, for example, powders, emulsions, suspensions, sprays, oils, ointments, fatty ointments, creams, pastes, gels, tablets, pills, capsules, and solutions.

One or both of the first and second agents described herein can be formulated for direct delivery to a site of inflammation. For example, where the patient is suffering from a disease that is associated with inflammation within the respiratory system (e.g., lung inflammation), the first and/or second agents can be formulated as porous particles for delivery by inhalation. For example, the agents can be administered directly as a powder (preferably in micronized form) or by atomizing solutions or suspensions which contain them. The first and/or second agents can be formulated as an aerosol. In some embodiments, the present agents can be delivered by the AERx Essence® pulmonary delivery device and AERx® system currently sold by Aradigm.

One or both of the first and second agents described herein can be incorporated into a nanoparticle (e.g., a therapeutic nanoparticle), which may improve the delivery profile and target specific tissues, such as lung tissue. The nanoparticles may be in the form of micron-scale dry powders and nanoparticles as described in Sung et al. (*Trends Biotechnol.*, 25(12):563-570, 2007) or Azarmi et al. (*Advanced Drug Delivery Reviews*, 60(8):863-876, 2008) and may be lipid-based (e.g., liposomes or micelles) or non-lipid-based. In addition to liposomes and micelles, the first and second agents can also be associated with (e.g., covalently or non-covalently bound to) mesoporous silica nanoparticles (MSNs), poly propyleneimine (PPI), quantum dots, and polymers (e.g., polyethylene glycol). Each of these delivery vehicles including the first and second agents described herein are within the scope of the present invention, and the methods of treatment described herein can employ administration of the first and/or second agents in association with any such delivery vehicle. Methods of preparing and administering nanoparticles are well known in the art (see, e.g., Garbuzenko et al., *Cancer Biol. Med.*, 11(1):44-55, 2014).

We tend to use the term "disease" to describe a malady, and as used herein, the term "disease" encompasses various maladies which may be more frequently described in the literature as being an illness, condition, disorder, infection, syndrome, or the like.

The present compositions and methods can incorporate a third agent, such as a cytochrome P450 enzyme inducer (e.g., rifampicin, phenobarbital, carbamazepine, and phenytoin), an inhibitor of CYP3A4, or dual inhibitors of CYP3A4 and CYP1A2 (e.g., erythromycin, ketoconazole, fluvoxamine, enoxacin, and cimetidine). Conventionally, these agents are avoided in conjunction with roflumilast, as they are thought to increase the patient's systemic exposure to roflumilast and therefore result in increased adverse reactions. However, the risks associated with such concurrent use are diminished in the context of the present invention, where compositions and treatments include an inhibitor of PDE4B2.

EXAMPLES

We wanted to better understand how PDE4B is up-regulated in the context of the complex pathogenesis and medications of COPD and whether counteracting this upregulation could help improve the efficacy and possibly ameliorate the tolerance of roflumilast. In the studies below, we show that roflumilast synergizes with nontypeable *Haemophilus influenzae* (NTHi), a major bacterial cause of COPD exacerbation, to up-regulate PDE4B2 expression in human airway epithelial cells in vitro and in vivo. Up-regulated PDE4B2 contributes to the induction of certain important chemokines in both enzymatic activity-dependent and -independent manners. We also found that the protein kinase A catalytic subunit β (PKA-Cβ) and nuclear factor-κB (NF-κB) p65 subunit were required for the synergistic induction of PDE4B2. PKA-Cβ phosphorylates p65 in a cAMP-dependent manner. Moreover, Ser276 of p65 is critical for mediating the PKA-Cβ-induced p65 phosphorylation and the synergistic induction of PDE4B2. Collectively, our data unveil a novel mechanism underlying synergistic upregulation of PDE4B2 via a cross-talk between PKA-Cβ and p65 and provide a basis for developing new therapeutic strategies to improve the efficacy of PDE4 inhibitors such as roflumilast (see FIG. 1).

The following materials and methods were employed in the Examples described below.

Reagents and antibodies. Actinomycin D and protease inhibitor cocktail (PIC) were purchased from Sigma-Aldrich. Myristoylated PKA inhibitor and IKKβ inhibitor IV were purchased from EMD Millipore. Roflumilast was purchased from Santa Cruz Biotechnology. $N^6$-Phenyl-cAMP (6-Phe-cAMP), 8-pCPT-2'-O-Me-cAMP and Rp-8-CPT-cAMPS were purchased from BioLog. Forskolin was purchased from Enzo Life Sciences. Phos-tag Acrylamide was purchased from Wako Chemicals USA. Recombinant p65 protein was purchased from Active Motif. Recombinant PKA-Cβ protein was purchased from R&D Systems. Antibodies for PKA-Cβ (sc-904), p65 (sc-8008), β-actin (sc-8432), α-Tubulin (sc-69969), PDE4B (sc-25812) and TFIIB (sc-225) were purchased from Santa Cruz Biotechnology, and antibodies for PKA-Cα (#4782) and c-Rel (#4727) were purchased from Cell Signaling.

Bacterial strains and culture condition. Clinical isolates of NTHi strain 12 were used in this study (Ishinaga et al., *EMBO J.*, 26(4):1150-1162, 2007). Bacteria were grown on chocolate agar plates at 37° C. in an atmosphere of 5% $CO_2$ overnight and subsequently inoculated in brain heart infusion (BHI) broth supplemented with 3.5 μg/mL NAD and hemoglobin (BD Biosciences). After overnight incubation, the bacteria were subcultured into fresh broth and the log phase bacteria, monitored by measurement of optical density (OD) value, were washed and suspended in DMEM for in vitro cell experiments and in isotonic saline for in vivo animal experiments. For all in vitro experiments except the dose dependent experiment, NTHi was treated at multiplicity of infection (MOI) of 50.

Cell culture. All media described below were supplemented with 10% fetal bovine serum (Sigma-Aldrich). Human bronchial epithelial BEAS-2B cells were maintained in RPMI medium (Life Technologies) (ATCC® CRL-9609™). Human primary bronchial epithelial NHBE (Lonza) cells were maintained in bronchial epithelial growth media (BEGM) supplemented with BEGM SingleQuots (Jono et al., *J. Biol. Chem.* 277(47):45547-45557, 2002). BEAS-2B cells stably expressing human PDE4B2 (PDE4B2-stable cells) were obtained by plasmid transfection following Geneticin selection (300 μg/mL). Cells were cultured in a humidified atmosphere of 5% $CO_2$ at 37° C.

Real-time quantitative and semi-quantitative RT-PCR analyses. Total RNA was isolated with TRIZOL® reagent (Life Technologies) by following the manufacturer's instruction. For the reverse transcription reaction, TAQMAN® reverse transcription reagents (Life Technologies) were used as described previously. For quantitative RT-PCR analysis, PCR amplifications were performed by using SYBR™ Green Universal Master Mix (Life Technologies). In brief, reactions were performed in triplicate containing 2× Universal Master Mix, 1 μL of template cDNA, and 500 nM primers in a final volume of 12.5 μL, and the reactions were analyzed in a 96-well optical reaction plate (USA Scientific). Reactions were amplified and quantified by using a STEPONEPLUS™ Real-Time PCR System and the manufacturer's corresponding software (STEPONEPLUS™ Software v2.3; Life Technologies). The relative quantities of mRNAs were obtained by using the comparative Ct method and were normalized using human cyclophilin or mouse glyceraldehyde-3-phosphate dehydrogenase (GAPDH) as an endogenous control. For semi-quantitative RT-PCR analysis, PCR amplifications were performed with PRIMESTAR® Max polymerase (Takara) by following the manufacturer's instruction. The primer sequences used are listed in the following Table.

| Primer name | Forward (5'-3') | Reverse (5'-3') |
|---|---|---|
| For Q-PCD (Human) | | |
| Cyclophillin A | CGGGTCCTGGCATCTTGT (SEQ ID NO: 4) | GCAGATGAAAAACTGGGAACCA (SEQ ID NO: 5) |
| PDE4A | TGTCGGATTACGCTGGAGGC (SEQ ID NO: 6) | CATCGTGTCCACAGGGATGC (SEQ ID NO: 7) |
| PDE4B | CTATACCGATCGCATTCAGGTC (SEQ ID NO: 8) | CTGTCCATTGCCGATACAATT (SEQ ID NO: 9) |
| PDE4C | GACTTACCCCTCGACAACCA (SEQ ID NO: 10) | GAAAGTCTG CCTGCCAAGAG (SEQ ID NO: 11) |
| PDE4D | TGTGTGACAAGCACAATGCTTCC (SEQ ID NO: 12) | CACGATT GTCCTCCAAAGT GTCC (SEQ ID NO: 13) |
| CCL5 | CTACACCAGTGGCAAGTGC (SEQ ID NO: 14) | CTTTCGGGTGACAAAGACGAC (SEQ ID NO: 15) |
| CCL7 | GGCTTGCTCAGC CAGT TG (SEQ ID NO: 16) | GGTGGTCCTTCTGTAGCTCTC (SEQ ID NO: 17) |
| CXCL8/1L-8 | TCCTGATTTCTGCAAGCTCTG (SEQ ID NO: 18) | GTCCACTCTCAATCACTCTCAG (SEQ ID NO: 19) |
| CXCL10 | GAAATTAT TCCTGCAAGCCAATT TTG (SEQ ID NO: 20) | CCC TTCTTTTTCATTGTAGCAATG (SEQ ID NO: 21) |
| CXCL1 1 | ATTGTGTGCTACAGTTGT TCAAG (SEQ ID NO: 22) | TTTCTCAATATCTGCCACTTTCAC (SEQ ID NO: 23) |
| TNF-iα | CCCAGGCAGTCAGATCATCTT (SEQ ID NO: 24) | AGCTGCCCCTCAGCT TGA (SEQ ID NO: 25) |
| GM-CSF | AACAGTAGAAGTCATCTCAGAAATGTTTG (SEQ ID NO: 26) | GCTGGCCATCATGGT CAAG (SEQ ID NO: 27) |
| For Q-PCR (Mouse) | | |
| GAPDH | AC CCAGAAGACTGTGGATGG (SEQ ID NO: 28) | GGATGCAGGGATGATGT TCT (SEQ ID NO: 29) |
| PDE4B | GTAGAGGC CAGTTCCCATCA (SEQ ID NO: 30) | CCAACACCTAGTGCAGAGC (SEQ ID NO: 31) |

-continued

| Primer name | Forward (5'-3') | Reverse (5'-3') |
|---|---|---|
| For semi-Q-PCR (Human) | | |
| GAPDH | AAGGCTGGGCTCATTTG (SEQ ID NO: 32) | GTGTGGT GGGG GACTGAG (SEQ ID NO: 33) |
| PDE4B1 | ACCTTTCCTGGGCACAGCCAC (SEQ ID NO: 34) | GCAGCGTGCAGGCTGTTGTG (SEQ ID NO: 35) |
| PDE4B2 | AGCGGT GGTAGCGGTGAC TC (SEQ ID NO: 36) | GCAGCGTGCAGGCTGTTGTG (SEQ ID NO: 37) |
| PDE4B3 | CTCCACGCAGTT CACCAAGGAAC (SEQ ID NO: 38) | TGTGTCAGCTCCCGGTTCAGC (SEQ ID NO: 39) |
| PDE4B5 | ACTGTGAATTCTTTCAAAGGGATTTGTG (SEQ ID NO: 40) | GGTCTATTGTGAGAATATCCAGCCACAT (SEQ ID NO: 41) |

Plasmids, transfections and luciferase assay. The expression plasmids, constitutively active forms of IKKα (IKKα-CA, S176E/S180E) and IKKβ (IKKβ-CA, S177E/S181E) and a dominant negative form of IκBα (IκBα-DN, S32A/S36A) were previously described (Shuto et al., Proc. Natl. Acad. Sci. USA, 98(15):8774-8779, 2001; Ishinaga et al., supra). Luciferase reporter construct of NF-κB (pGL4.32) was purchased from Promega. Human PDE4B2, p65 (RelA) and PKA-Cβ1/2 cDNA sequences were generated and inserted into the BamHI and HindIII sites of the pcDNA3.1/mycHis(−) vector. Mutant p65 and PDE4B2-D392A were generated by using PRIMESTAR® Max (Takara). Empty vector was used as a control and was also added where necessary to ensure an equivalent amount of input DNA. All transient transfections were carried out in triplicate using TRANSIT-LT1® reagent (Minis) following the manufacturer's instruction.

siRNA-mediated knockdown. Human validated siRNA oligos were obtained from GE Healthcare (Negative Control, D001810-10; PDE4B, L007648-01; PKA-Cα, M004649-01; PKA-Cβ, M004650-00; p65, L003533-00; c-Rel, L004768-00). Cells were transfected with 50 nM siRNA using DHARMAFECT-4™ (Thermo Scientific) and collected or treated 48 h later. For the co-transfection of siRNA with DNA, cells were transfected with 10 nM siRNA using LIPOFECTAMINE™ 3000 (Life Technologies).

Subcellular fractionation. Cells were washed twice and corrected with ice cold PBS and centrifuged at 3,000×g for 5 min. The cells were then suspended with Buffer A (10 mM HEPES at pH7.4, 10 mM KCl, 0.1 mM EDTA, 0.1 mM EGTA, 1 mM DTT, supplemented with 1 mM $Na_3VO_4$ and PIC) and incubated on ice for 10 min (Schreiber et al., Nucleic Acids Res. 17(15):6419, 1989). The cells were lysed by adding NP40 (0.5%) and vortexing for 15 sec. then centrifuged at 3,000×g for 5 min before the supernatants were removed (cytosol fraction). Precipitates were resuspended in Buffer B (20 mM HEPES at pH7.5, 5 mM NaCl, 1 mM EDTA, mM EGTA, 1 mM DTT, supplemented with 1 mM $Na_3VO_4$ and PIC) and incubated on ice for 10 min. before vortexing and centrifuging at 16,000×g for 15 min to recover the supernatants (nuclear fraction).

Western blot. Whole-cell extracts and mouse lung tissue extracts were recovered with lysis buffer (50 mM Tris-HCl at pH7.4, 1% NP40, 0.25% deoxycholate, 150 mM NaCl, 1 mM EDTA, 1 mM NaF, supplemented with 1 mM $Na_3VO_4$ and PIC). For PDE4B protein, cell extracts were recovered with Buffer A as described above. Cell or tissue extracts were separated on 8% SDS-PAGE gels and transferred to polyvinylidene difluoride (PVDF) membrane (GE Healthcare Life Sciences). The membrane was blocked with a solution of TBS containing 0.1% Tween 20 (TBS-T) and 5% non-fat dry milk. The membrane was then incubated in a 1:1,000-1:2,000 dilution of a primary antibody in 5% BSA-TBS-T. After washing (×3) with TBS-T, the membrane was incubated with a 1:5,000 dilution of the corresponding secondary antibody in 2.5% non-fat dry milk-TBS-T. Respective proteins were visualized using Amersham ECL Prime Regent (GE Healthcare Life Sciences).

Immunoprecipitation. Cell extracts were incubated with 1 µg of primary antibodies overnight at 4° C., followed by a 2 h incubation with protein G PLUS-agarose beads (Santa Cruz Biotechnology). Immunoprecipitates were then suspended in a sample buffer, separated on 8% SDS-PAGE gels, transferred to PVDF membrane, and detected by immunoblot analysis as described above.

PDE4 activity. PDE4 activity in whole-cell extracts from the cells transfected with PDE4B2 constructs were measured by using a cyclic nucleotide PDE assay kit (Enzo Life Sciences) following the manufacturer's instructions. PDE4 activity was estimated from the difference between total and roflumilast-resistant PDE activity.

Phos-tag PAGE. Recombinant p65 proteins or nuclear extracts recovered without EDTA/EGTA were separated by SDS-PAGE, with 6% gels containing 50 µM $Mn^{2+}$-Phos-tag Acrylamide and transferred to PVDF membrane according to the manufacture's instructions (Kinoshita et al., Mol. Cell. Proteomics 5(4):749-757, 2006.

In vitro kinase assay. Recombinant p65 protein (70 ng) and recombinant PKA-Cβ (50 ng) were mixed in kinase assay buffer (20 mM HEPES at pH7.5, 1 M $MgCl_2$, 1 mM DTT, 10 mM ATP) and incubated at 30° C. for 0.5 h. The reaction was stopped by adding 4×SDS sample buffer (0.24 M Tris-HCl at pH 6.8, 40% Glycerol, 8% SDS, 20% 2-Mercaptoehanol, 0.04% Bromophenol blue).

Mice and animal experiments. For NTHi-induced inflammation in C57BL/6J mice (7 weeks old), anaesthetized mice were intratracheally inoculated with NTHi at a concentration of $5×10^7$ CFU per mouse and saline was inoculated as control. The inoculated mice were then sacrificed 5 h after NTHi inoculation. For inhibition studies, the mice were pretreated with roflumilast intraperitoneally 2 h before NTHi inoculation. All animal experiments were approved by the Institutional Animal Care and Use Committee (IACUC) at Georgia State University.

Immunofluorescent staining. Formalin-fixed paraffin-embedded mouse lung tissue was sectioned (4 µm) and PDE4B protein was detected using a rabbit anti-PDE4B and an FITC-conjugated goat anti-rabbit IgG (Santa Cruz Biotechnology). Stained sections were then imaged, and images were recorded under light- and fluorescence-microscopy systems (AxioVert 40 CFL, AxioCam MRC, and AxioVision LE Image system, Carl Zeiss).

Statistical analysis. All experiments were repeated at least three times with consistent results. Data were shown as mean±SD. Statistical analysis was assessed by unpaired two-tailed Student's t-test and p<0.05 was considered statistically significant.

Figure 2:
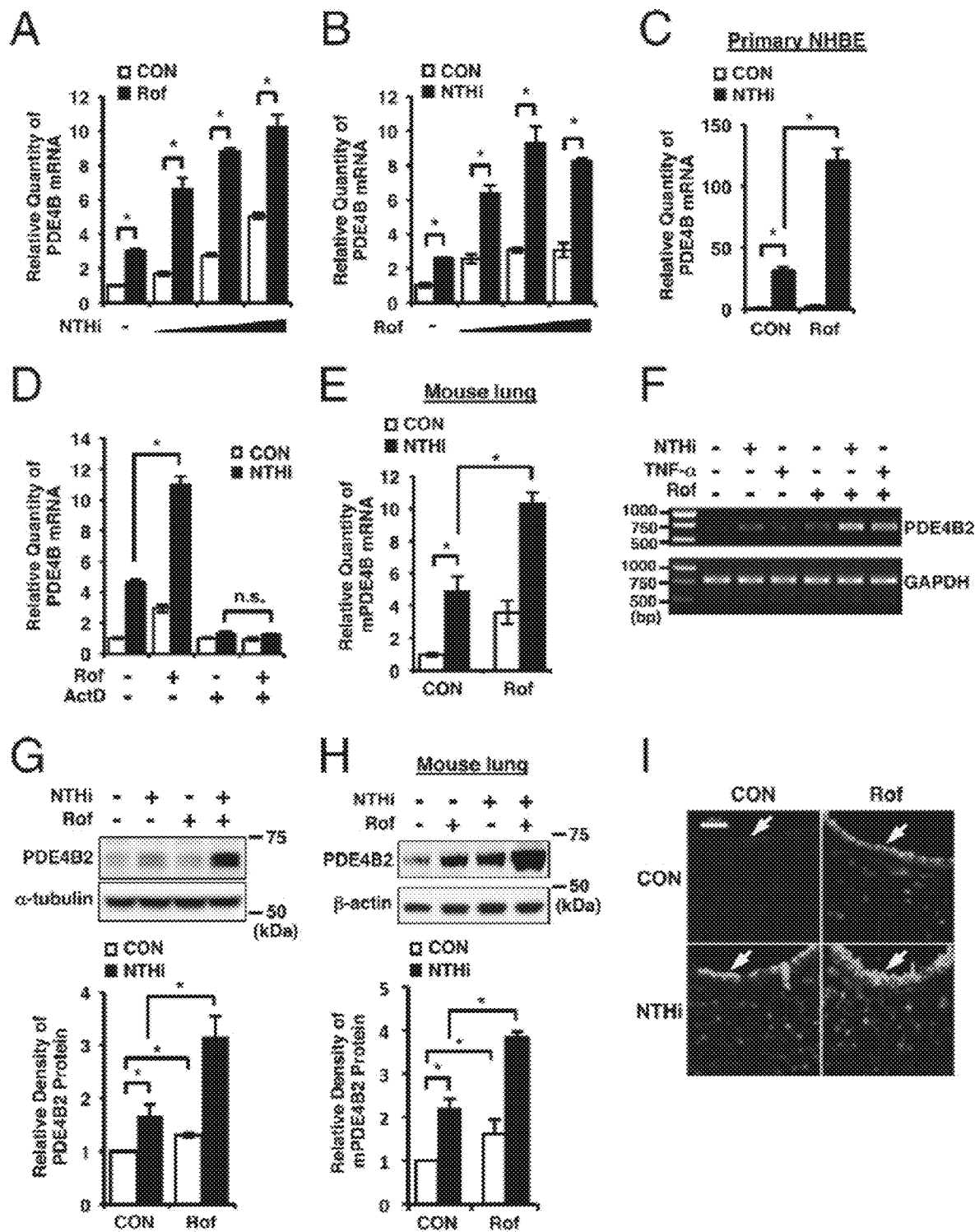
FIGS. 2A-2I show results indicating that roflumilast synergizes with NTHi to up-regulate PDE4B2 expression in vitro and in vivo.

Example 1: Roflumilast synergizes with NTHi to up-regulate PDE4B2 expression in vitro and in vivo. Because the expression of PDE4 isoforms is induced by PDE4 inhibitors (Campos-Toimil et al., *Br. J. Pharmacol.* 154(1): 82-92, 2008; Dlaboga et al., *Brain Res.*, 1096(1):104-112, 2006; Giorgi et al., *Behav. Brain Res.* 154(1);99-106, 2004) and PDE4B is also induced by NTHi (Komatsu et al., *Nat. Commun.* 4:1684, 2013), we sought to determine if roflumilast synergizes with NTHi to induce PDE4B expression in human airway epithelial cells (BEAS-2B cells). As shown in FIGS. 2A and B, roflumilast indeed synergized with NTHi to up-regulate PDE4B expression at the mRNA level in human bronchial epithelial BEAS-2B cells in a dose-dependent manner as assessed by quantitative PCR (Q-PCR) analysis. A similar result was also confirmed in primary normal human bronchial epithelial (NHBE) cells (FIG. 2C). We also analyzed the expressions of other PDE4 family members under the same condition and found that PDE4A and 4C were not up-regulated by NTHi or roflumilast. PDE4D was up-regulated by NTHi or roflumilast but no significant synergistic effect was observed, suggesting that PDE4B is specifically regulated by NTHi and roflumilast in a synergistic manner. To further determine whether the synergistic induction of PDE4B occurs at the transcriptional level, we treated BEAS-2B cells with actinomycin D (ActD), a transcriptional inhibitor (believed to inhibit transcription by binding DNA at the transcription initiation complex and preventing elongation of RNA by RNA polymerase; Sobell, *Proc. Natl. Acad. Sci. USA*, 82(16):5328-5331, 1985). ActD completely abrogated the PDE4B induction by NTHi and roflumilast, suggesting that the synergistic induction of PDE4B occurs at the transcriptional level (FIG. 2D). We next determined if roflumilast synergizes with NTHi to up-regulate PDE4B expression in vivo. Consistent with the in vitro results, roflumilast synergistically enhanced NTHi-induced PDE4B expression at mRNA level in mouse lungs (FIG. 2E).

We also performed a semi-quantitative RT-PCR analysis to determine which PDE4B isoforms are up-regulated by NTHi and roflumilast. The human PDE4B gene encodes a number of distinct isoforms, so-called long forms PDE4B1 and PDE4B3, short form PDE4B2, and super-short form PDE4B5 (Huston et al., *Biochem. J.* 328(Pt 2):549-558, 1997; Cheung et al., *J. Pharmacol. Exp. Ther.* 322(2):600-609, 2007; Bolger et al., *Mol. Cell Biol.* 13(10):6558-6571, 1993; Colicelli et al., *Proc. Natl. Acad. Sci. USA* 86(10): 3599-3603, 1989; Zhang, *Curr. Pharm. Des.* 15(14):1688-1698, 2009). We were unable to examine another long form, PDE4B4, because its cDNA has been Cloned only in rat and this isoform appears not to be encoded by human genomes (Shepherd et al., *Biochem. J.*, 370(Pt 2):429-438, 2003). As shown in FIG. 2F, the expression of PDE4B2 was synergistically up-regulated by roflumilast and NTHi or TNF-α. The amplified PCR bands for PDE4B1, PDE4B3 and PDE4B5 were not detected even after 40 cycles of amplification in BEAS-2B cells.

The synergistic induction of PDE4B2 expression was also verified at the protein level in vitro and in vivo (FIG. 2G-I). Western blot analyses in airway epithelial cell extracts and mouse lung tissue extracts revealed that NTHi and roflumilast induced an increase in the ~70-kDa PDE4B isoform, which comigrates with overexpressed human PDE4B2 protein (FIGS. 2G and 2H) (Huston et al., *Biochem. J.* 328(Pt 2):549-558, 1997; Marquette et al., *Nat. Struct. Mol. Biol.*, 18(5):584-591, 2011; Millar et al., *Science*, 310(5751):1187-1191, 2005; Yougbare et al., *Am. J. Physiol. Lung Cell. Mol. Physiol.*, 301(4):L441-L450). Immunofluorescent staining showed that the high intensity of PDE4B immunofluorescence signals was largely detected in bronchial epithelium of mouse lung tissues (FIG. 2I, arrows). Consistently, the PDE4B enzyme activity was also increased due to the up-regulation of PDE4B2 protein expression caused by roflumilast and NTHi. Together, our data suggest that roflumilast synergizes with NTHi to specifically up-regulate PDE4B2 expression at both the mRNA and protein levels in vitro and in vivo.

Example 2: PDE4B2 is required for NTHi-induced expression of pro-inflammatory mediators. Next, we sought to determine the role of PDE4B2 expression in NTHi-induced inflammatory response in human airway epithelial cells. Pro-inflammatory mediators including cytokines and chemokines play critical roles in the recruitment and activation of leukocytes from the circulation to the lung in airway inflammatory diseases (Donnelly and Barnes, *Trends Pharmacol. Sci.*, 27(10):546-553, 2006; Le et al., *Cell Mol. Immunol.*, 1(2):95-104, 2004; Quint and Wedzicha, *J. Allergy Clin. Immunol.*, 119(5):1065-1071, 2007. Airway epithelial cells are the important sources of pro-inflammatory mediators induced by bacterial pathogens (Hallstrand et al., *Clin. Immunol.*, 161(1):1-15, 2014). Thus, we first determined if NTHi induces the expression of a number of key pro-inflammatory mediators that have been shown to be critical in the pathogenesis of COPD. We found that NTHi significantly up-regulated the expression of CCL5, CCL7, CXCL10, CXCL11, Interleukin-8 (IL-8/CXCL8), granulocyte-macrophage colony-stimulating factor (GM-CSF) and TNF-α in BEAS-2B cells. Interestingly, roflumilast inhibited NTHi-induced expression of these pro-inflammatory mediators to various extents. Roflumilast markedly inhibited the induction of TNF-α and GM-CSF, but modestly suppressed the induction of CCL5, CCL7 and IL-8. In contrast, it exhibited almost no inhibitory effect on CXCL10 and CXCL11 induction even at higher concentration. These interesting results have led us to postulate that the low or limited efficacy of roflumilast in suppressing these pro-inflammatory mediators may be attributed to the up-regulated expression of PDE4B2 by roflumilast in the presence of NTHi. We thus determined the contribution of PDE4B2 by assessing the effects of PDE4B2 depletion using PDE4B siRNA on induction of these pro-inflammatory mediators by NTHi. As expected, PDE4B siRNA markedly depleted PDE4B2 expression in BEAS-2B cells (FIG. 3). PDE4B2 depletion further significantly inhibited the induction of CCL5, CCL7, CXCL10 and CXCL11 (Group A) that were modestly or minimally inhibited by roflumilast alone. In contrast, PDE4B2 depletion only minimally affected the induction of IL-8, GM-CSF and TNF-α (Group B) that were modestly or markedly inhibited by roflumilast alone.

PDE4D was also up-regulated by NTHi and roflumilast, and previous studies have suggested that PDE4D has a different and non-redundant role from PDE4B (Ariga et al., *J. Immunol.*, 173(12):753107538, 2004; Blackman et al., *J. Biol. Chem.*, 286(14):12590-12601, 2011). We thus also evaluated the effect of PDE4D depletion on NTHi-induced expression of pro-inflammatory mediators. The induction of chemokines in Group A was attenuated by PDE4D depletion but to a much lesser extent compared to PDE4B depletion.

The induction of chemokines and cytokines in Group B was not affected or even slightly enhanced by PDE4D depletion. Collectively, these results suggest that different pro-inflammatory mediators are differentially regulated by PDE4B and 4D and the expression of PDE4B plays a more crucial role in NTHi-induced expression of CCL5, CCL7, CXCL10 and CXCL11 in bronchial epithelial cells.

To further confirm the role of PDE4B2 up-regulation in NTHi-induced expression of chemokines, we developed cells stably overexpressing wild-type PDE4B2 (PDE4B2-stable cells). PDE4B2 expression in PDE4B2-stable cells was higher in mock-transfected (Mock) cells (FIG. 4A). NTHi-induced expression of CCL5, CCL7, CXCL10 and CXCL11 was significantly enhanced in PDE4B2-stable cells compared to Mock cells (FIG. 4B). Interestingly, roflumilast was unable to fully inhibit the NTHi-induced expression of these chemokines in PDE4B2-stable cells even at the highest concentration tested (10 µM). Of note, the NTHi-induced expression of CXCL10 and CXCL11 was even slightly enhanced by a lower dose of roflumilast (<1 µM) in PDE4B2-stable cells (FIG. 4B). In line with the results from PDE4B depletion, PDE4B2 overexpression did not markedly increase the expression of IL-8, GM-CSF and TNF-α induced by NTHi in the presence of roflumilast. Together, these results suggest that PDE4B2, synergistically up-regulated by NTHi and roflumilast, may contribute, at least in part, to the decreased efficacy of roflumilast in suppressing CCL5, CCL7, CXCL10 and CXCL11 induction in bronchial epithelial cells.

It has been previously shown that the enzymatic activity of PDE4 is critical for regulating inflammatory responses (Bender and Beavo, *Pharmacol. Rev.*, 58(3):488-520, 2006; Lipworth, *Lancet*, 365(9454):167-175, 2005; Karlsson et al., *Int. Arch. Allergy Immunol.*, 107(1-3):426-426, 1995; Michalski et al., *Clin. Pharmacol. Ther.*, 91(1):134-142, 2012). However, our data revealed that up-regulated PDE4B2 induces certain pro-inflammatory mediators in a manner that cannot be overcome by high doses of roflumilast (up to 10 µM; a very high level of this drug as the $IC_{50}$ has been estimated at less than 1 nM) (Bender and Beavo, supra). These very interesting but rather unexpected results thus led us to hypothesize that PDE4B2 may regulate the expression of these chemokines at least in part independently of its well-known enzymatic activity by, e.g., acting as an adaptor protein. To test this hypothesis, we compared the effects of expressing wild-type PDE4B2 (PDE4B2-WT) and a catalytically inactive form of PDE4B2 (PDE4B2-D392A) (Mongillo et al., *Circ. Res.*, 95(1):67-75, 2004; Xu et al., *Science*, 288(5472):1822-1825, 2000) on NF-κB-dependent promoter activity and chemokine induction. Both PDE4B2-WT and PDE4B2-D392A were equally expressed in transfected BEAS-2B cells, and PDE4 activity was significantly lower in the cells transfected with the PDE4B2-D392A mutant than in cells transfected with PDE4B2-WT. We found that PDE4B2-WT markedly enhanced a constitutively active form of the inhibitor of NF-κB (IκB) kinase β (IKKβ-CA)-induced NF-κB promoter activity in a dose-dependent manner and also enhanced IKKβ-CA-induced Group A-chemokine expression. Interestingly, PDE4B2-D392A also enhanced IKKβ-CA-induced NF-κB promoter activity and chemokine expression although to a lesser extent compared with PDE4B2-WT. Moreover, roflumilast (up to 10 µM) was unable to fully inhibit the IKKβ-CA-induced NF-κB promoter activity and Group A-chemokine expression in the cells transfected with PDE4B2-D392A. Together, these results suggest PDE4B2 enhances the inflammatory response in both PDE enzymatic activity-dependent and -independent manners, which may contribute to the tolerance to roflumilast.

Example 3: PKA-Cβ but not PKA-Cα is required for synergistic induction of PDE4B2. To investigate the mechanism underlying the synergistic induction of PDE4B2, we first examined whether cAMP, which is increased by roflumilast, is involved in the synergistic induction of PDE4B2. Forskolin (FSK), a potent cAMP elevator, synergized with NTHi to up-regulate PDE4B2 expression, suggesting that cAMP is involved in the synergistic induction of PDE4B2 in BEAS-2B cells. Thus, we further investigated the involvement of two ubiquitously expressed intracellular cAMP effectors, PKA and an exchange protein directly activated by cAMP (Epac). A specific PKA inhibitor (PKI) significantly suppressed the synergistic induction of PDE4B2 by NTHi and roflumilast. This inhibitor, the polypeptide TTYAD-FIASGRTGRRNAIHD (SEQ ID NO:3), can be readily synthesized and is also available from Santa Cruz Biotechnologies. PKI and active fragments or variants thereof (e.g., polypeptides that are at least 80% (e.g., 85%, 90%, or 95%) identical thereto, can be used in the present compositions and methods to inhibit PKA-Cβ. Consistent with this result, a PKA-selective activator 6-Phe-cAMP, which does not activate Epac, synergistically enhanced NTHi-induced PDE4B2 expression. In contrast, the Epac-selective activator 8-pCPT-2'-O-Me-cAMP did not markedly synergize with NTHi to induce PDE4B2 expression. These results suggest that cAMP-dependent activation of PKA but not Epac is required for the synergistic induction of PDE4B2 in bronchial epithelial cells.

PKA is a tetrameric enzyme consisting of two catalytic (C) and two regulatory (R) subunits. Binding of cAMP to R subunits results in relief of R subunit inhibition of the C subunits, which then phosphorylate a wide variety of protein substrates (Krebs and Beavo, *Annu. Rev. Biochem.*, 48:923-959, 1979; Levitan, *Anna. Rev. Physiol.*, 56:193-212, 1994; Montminy et al., *Trends Neurosci.*, 13(5):184-188, 1990; Gamm et al., *J. Biol. Chem.*, 271(26):15736-15742, 1996; Padmanabhan et al., *J. Biol. Chem.*, 288(20):14158-14169, 2013). Three C subunit isoforms, PKA-Cα, -Cβ and -Cγ, have been identified in humans, although Cγ is testis specific (Beebe et al., *Mol. Endocrinol.*, 4(3):465-475, 1990). We next determined which PKA isoform is involved in the synergistic induction of PDE4B2 by depleting PKA-Cα and -Cβ using specific siRNAs. Western blot analysis revealed that the protein expression of PKA-Cα and Cβ was efficiently and selectively decreased in siRNA-transfected cells, respectively (FIG. 5). Interestingly, the synergistic induction of PDE4B2 by NTHi and roflumilast was significantly attenuated by PKA-Cβ depletion, whereas only a slight suppression was observed in PKA-Cα-depleted cells. Next, we determined the effect of PKA-Cβ depletion on the up-regulation of pro-inflammatory mediators induced by NTHi in the presence of roflumilast. The inhibitory effect of PICA-Cβ depletion on the expression of pro-inflammatory mediators is highly Consistent with that of PDE4B2 depletion, except that PKA-Cβ depletion attenuated CCL7 and GM-CSF up-regulation to a greater extent than PDE4B2 depletion. These results suggest that PICA-Cβ acts as a key positive regulator in the synergistic up-regulation of PDE4B2 and pro-inflammatory mediators induced by NTHi and roflumilast. Some of the NTHi-induced pro-inflammatory mediators were even increased by PKA-Cα depletion, which is line with the anti-inflammatory effects of PKA-Cα reported in other cell types (Ollivier et al., *J. Biol. Chem.*, 271(34):20828-20835, 1996).

Since it has been shown that the cAMP response element (CRE) plays a particularly important role in up-regulating PDE4B2 expression in rat neurons (D'Sa et al., *J. Neurochem.*, 81(4):745-757, 2002), we examined the involvement of CRE-binding protein (CREB) and activating transcription factor 1 (ATF1), two ubiquitously expressed PKA-dependent transcription factors (Mayr and Montminy, *Nat. Rev. Mol. Cell Biol.*, 2(8):599-609, 2001), on the synergistic induction of PDE4B2 by NTHi and roflumilast in BEAS-2B cells. Interestingly, depletion of either CREB or ATF1 decreased the synergistic induction of PDE4B2 but to a much lesser extent compared to PKA-Cβ depletion. These results suggest that other downstream molecules of PKA-Cβ may play a more important role in the synergistic induction of PDE4B2 in bronchial epithelial cells. Nonetheless, our data suggest that PKA-Cβ but not PKA-Cα is crucial for the synergistic induction of PDE4B2 by NTHi and roflumilast.

Example 4: IKKβ-p65 but not c-Rel is required for synergistic induction of PDE4B2. Because NTHi is known as a potent activator of IKKβ(3 (also known as IKK2), leading to the activation of NF-κB-dependent inflammatory response (Shuto et al., *Proc. Natl. Acad. Sci. USA*, 98(15):8774-8779, 2001; Oeckinghaus and Ghosh, *Cold Spring Harb. Perspect. Biol.*, 1(4):a000034, 2009; Chen et al., *Biochem. Biophys. Res. Commun.*, 324(3):1087-1094, 2004), we examined the requirement of IKKβ-NF-κB signaling in the synergistic induction of PDE4B2. We first evaluated the role of IKKβ. An IKKβ inhibitor significantly inhibited the synergistic induction of PDE4B2 by NTHi and roflumilast, but did not affect the induction of PDE4B2 by roflumilast alone. To further determine if the activation of IKKβ indeed synergizes with roflumilast to induce the synergistic up-regulation of PDE4B2, BEAS-2B cells were transfected with the constitutively active form of IKKα (IKKα-CA) and IKKβ (IKKα-CA). We found that PDE4B2 expression was synergistically enhanced by roflumilast or a PKA activator 6-Phe-cAMP in IKKβ-CA- but not IKKα-CA-transfected cells. In addition, we also demonstrated that the expression of a dominant-negative mutant of IκBα (IκBα-DN), the downstream molecule of IKKβ, completely blocked IKKβ-CA-induced PDE4B2 expression and the synergistic induction of PDE4B2 by roflumilast in IKKβ-CA-transfected cells. These results suggest that IKKβ-IκBα signaling pathway is required for the synergistic induction of PDE4B2.

IκBα prevents the activation and nuclear translocation of NF-κB complexes including p65 and c-Rel, which have been previously known to be activated by PKA-Cα and PKA-Cβ, respectively (Gerlo et al., *Cell Mol. Life Sci.*, 68(23):3823-3841, 2011; Yu et al., *J. Mol. Med.* (Berl.), 82(9):621-628, 2004; Zhong et al., *Cell*, 89(3):413-424, 1997; Zhong et al., *Mol. Cell.*, 1(5):661-671, 1998). Thus, we first investigated if NTHi induces nuclear translocation of p65 and c-Rel. We found that both p65 and c-Rel were translocated to the nucleus within 60 min after the NTHi treatment in BEAS-2B cells. These results led us to further determine the requirement of p65 and c-Rel for the synergistic induction of PDE4B2 by using siRNA to selectively deplete p65 or c-Rel. We found that depletion of p65, but not c-Rel, significantly inhibited the synergistic induction of PDE4B2 by both NTHi and roflumilast or PDE4B2 induction by NTHi alone but not by roflumilast alone, thereby indicating an important role of p65 in NTHi-induced PDE4B2 expression. We further determined if overexpression of p65 synergizes with roflumilast to induce PDE4B2. Roflumilast indeed synergistically enhanced PDE4B2 expression in p65-transfeceted cells. Collectively, our data demonstrate that the IKKβ-IκBα-p65 signaling pathway is required for the synergistic induction of PDE4B2 in bronchial epithelial cells.

Example 5: PKA-β phosphorylates p65. To further determine how PKA-Cβ interacts with p65 and how these molecules synergize to up-regulate PDE4B2 expression, we first investigated if p65 is physically associated with PKA-Cβ by performing co-immunoprecipitation experiments. We found that p65 and PKA-Cβ were physically associated with each other in BEAS-2B cells transfected with both p65 and PKA-Cβ. Moreover, their interaction was enhanced by co-treatment of roflumilast with NTHi. We found that roflumilast did not affect the nuclear expression level of p65 or PKA-Cβ in BEAS-2B cells. Thus, we next examined if PKA-Cβ affects p65 phosphorylation. Phosphorylation at multiple residues of p65 has been shown to regulate various functions of p65, such as DNA binding and transcriptional activities (Huang et al., *Cell Signal*, 22(9):1282-1290, 2010; Chaturvedi et al., *Oncogene*, 30(14):1615-1630, 2011). However, the role of PKA-Cβ in regulating p65 phosphorylation remains unknown. To evaluate p65 phosphorylation, we performed phosphate-affinity (Phos-tag) PAGE, a novel phosphate-binding tag-based method that has been developed to specifically decrease the migration speed of phosphorylated proteins so that the phosphorylated protein can be separated from non-phosphorylated protein (Kinoshita et al., *Mol. Cell. Proteomics*, 5(4):749-757, 2006). Co-treatment of roflumilast with NTHi induced phosphorylation of p65, which was inhibited by Rp-8-CPT-cAMPS, a specific inhibitor of cAMP-dependent PKA activation. PKA-Cβ depletion or H89 treatment exhibited similar inhibitory effects. Consistent with these results, a cAMP-dependent PKA-selective activator 6-Phe-cAMP also induced this phosphorylation. Of note, NTHi alone did not induce the similar phosphorylation in BEAS-2B cells, suggesting that PKA-Cβ activation by cAMP is required for p65 phosphorylation. We also found that the overexpression of PKA-Cβ1, the major subtype of Cβ in BEAS-2B cells, induced the phosphorylation of p65, which was inhibited by H89, but not by a p38 inhibitor (SB203580) or an ERK inhibitor (PD98059). These results suggest that PKA-Cβ1 directly phosphorylates p65, independently of activation of p38, ERK or their downstream kinase MSK1 (mitogen- and stress-activated kinase 1) that has been shown to phosphorylate p65 (Gerits et al., *Cellular Signalling*, 20(9):1592-1607, 2008; Joo and Jetten, *J. Biol. Chem.*, 283(24):16391-16399, 2008; Reber et al., *PloS one* 4(2):e4393, 2009). Searching for a PKA consensus phosphorylation sequence (RRXS/T) revealed that the serine 276 residue (Ser276) is a potential PKA phosphorylation site (Songyang et al., *Curr. Biol.*, 4(11):973-982, 1994), which is in line with previous studies showing that PKA-Cα phosphorylates p65 at Ser276 residue (Zhong et al., 1998 and Zhong et al., 1998, supra). To determine if p65 is also phosphorylated by PKA-Cβ at Ser276, BEAS-2B cells were transfected with the phosphorylation-deficient mutant (S276A) of p65 and analyzed by Phos-tag PAGE. The p65 constructs with mutation of other serine residues (S468A, S529A and S536A) known to be phosphorylated by other kinases were also analyzed. The intensity ratio of PKA-Cβ-induced phosphorylation was decreased in S276A- and S536A-transfected cells compared to the wild-type p65-transfected cells. To further determine the functional involvement of p65 phosphorylation at these residues in PDE4B2 induction, we examined PDE4B2 expression in the cells transfected with these different p65 phosphorylation site mutants. Roflumilast and NTHi synergistically enhanced PDE4B2 expression in the cells transfected with p65 mutants S468A, S529A and S536A but not S276A. We next determined the effect of Ser276 phosphorylation by PKA-Cβ on the transcriptional activity of p65 by performing the NF-κB promoter activity analysis. Co-transfection with PKA-Cβ1 significantly enhanced the p65-induced NF-κB promoter activity, which was abrogated by co-expressing the S276A mutant of p65. Together, these results suggest that roflumilast and NTHi increase the physical interaction of PKA-Cβ with p65, which in turn leads to the phosphorylation of p65 at Ser276 and subsequent up-regulation of p65-dependent transcriptional activity.

Example 6: Dexamethasone suppresses PDE4B induction by NTHi and Rof and improves the efficacy of Rof in suppressing NTHi-induced inflammation in lung epithelial cells in vitro and in mouse lung. We pre-treated BEAS-2B cells with Rof (1 µM), FSK (1 µM), Iso (0.1 µM) and DEX (10 nM) for 1 h followed by 1.5 h stimulation with NTHi, and PDE4B mRNA expression was analyzed by Q-PCR (FIGS. 7A and 7B). We also pre-treated BEAS-2B cells with Rof (0.1 µM) and DEX (6.5 nM) for 1 h followed by 1.5 h stimulation with NTHi, and PDE4B2 mRNA expression was analyzed by semi-quantitative RT-PCR (FIG. 7C). To assess protein expression, BEAS-2B cells were pre-treated with Rof (0.1 µM) and DEX (100 nM) for 1 h followed by a 5 h stimulation with NTHi, and PDE4B protein expression was analyzed by immunoblot (FIG. 7D). Each target data were normalized with NTHi treated. Data are mean±SD (n=3); *p<0.05 vs NTHi; †p<0.05 vs Rof+NTHi. Mice were inoculated with Rof (5 mg/kg i.p.) and/or DEX (2 mg/kg i.p.) for 2 h, followed by intratracheally inoculation with NTHi ($5 \times 10^7$ CFU/lung) (FIGS. 7E and 7G). After 5 h, mRNA expression in lung tissues were analyzed by Q-PCR for assessing the expression of PDE4B or various proinflammatory mediators and lung tissues were stained against PDE4B (Magnification ×200, Scale bar, 100 µm) (FIG. 7F) and assessed for inflammation using H&E staining (FIG. 7H).

Commentary: PDE4B has been shown to be up-regulated by various inflammatory stimuli, which plays a critical role in mediating inflammatory response (Gobejishvili et al., *Am. J. Physiol. Gastrointest. Liver Physiol.*, 294(4):G718-G724, 2008; Gobejishvili et al., *J. Pharmacol. Exp. Ther.*, 337(2): 433-443, 2011; Jin and Conti, *Proc. Natl. Acad. Sci. USA*, 99(11):7628-7633, 2002; Ma et al., *Mol. Pharmacol.*, 55(1): 50-57, 1999; Cohen et al., *J. Biol. Chem.*, 275(15):11181-11190, 2000; Borysiewicz et al., *Metab. Brain Dis.*, 24(3): 481-491, 2009; Christiansen et al., *Neurochem. Int.*, 59(6): 837-846, 2011). We recently also found that PDE4B is induced by bacterium NTHi (Komatsu et al., *Nat. Commun.*, 41684, 2013). It is also known that the expression level of PDE4 isoforms is induced by cAMP elevators including PDE4 inhibitor itself (Jin and Conti, supra; Mehats et al., *Endorinology*, 140(7):3228-3237, 1999; Campos-Toimil et al., *Br. J. Pharmacol.*, 154(1):82-92, 2008; D'Sa, supra; Dlaboga et al., *Brain Res.*, 1096(1):104-112, 2006; Giorgi et al., *Behav. Brain Res.*, 154(1):99-106, 2004), which is believed to be important in the negative feedback regulation of cAMP signaling. However, it remains unclear how PDE4 is regulated in the presence of both bacterial pathogen and cAMP elevators. In this study, we showed for the first time that roflumilast (a clinically approved PDE4 inhibitor for COPD exacerbation), synergizes with NTHi (a major bacterial cause of COPD exacerbation) to induce PDE4B2 expression in the context of the complex pathogenesis and medications of COPD, via a cross-talk between cAMP/PKA-Cβ and p65 (FIG. 1). The synergistic induction of PDE4B2 was also observed in the presence of other inflammatory stimuli, such as TNF-α and IL-1β, and cAMP elevators. PDE4B2 expression plays a critical role in NTHi-induced expression of chemokines CCL5, CCL7, CXCL10 and CXCL11, which have previously been shown to be crucial in the pathogenesis of COPD exacerbation. These chemokines are increased in induced sputum, bronchoalveolar lavage (BAL) fluid or peripheral airways in patients with COPD (Saetta et al., *Am. J. Resp & Crit. Care Med.*, 165(10):1404-1409, 2002; Fujimoto et al., *Eur. Respiratory J.*, 25(4):640-646, 2005; Costa et al., *Chest*, 133(1):26-33, 2008; Hacievliyagil et al., *Respiratory Med.*, 100(5):846-854, 2006; Frankenberger et al., *Mol. Med.*, 17(7-8):762-770, 2011) and play important roles in the recruitment of macrophages, $CD8^+$ T cells, B cells, eosinophils and neutrophils into the airway lumen (Donnelly and Barnes, *Trends Pharmacol Sci.*, 27(10):546-553, 2006; Le et al., *Cell Mol. Immunol.*, 1(2):95-104, 2004; Quint and Wedzicha, *J. Allergy Clin. Immunol.*, 119(5):1065-1071, 2007; Michalec et al., *J. Immunol.*, 168(2):846-852, 2002; Gross, *Chest*, 142(5):1300-1307, 2012).

The second major finding of this study is that PDE4B2 regulates the expression of certain chemokines in both an enzymatic activity-dependent and -independent manner. This may lead to the reduced efficacy of roflumilast in suppressing inflammation under certain clinical conditions due to the synergistically up-regulated PDE4B2. For example, we observed that the effect of roflumilast in suppressing NTHi-induced CCL5, CCL7, CXCL10 and CXCL11 (named Group A-chemokines) is less than its effect in suppressing some other pro-inflammatory mediators such as GM-CSF and TNF-α in bronchial epithelial cells. In addition, roflumilast became more efficacious in suppressing Group A-chemokines in PDE4B-depleted but not in PDE4D-depleted cells. Consistent with these results, roflumilast (even at 10 µM) was unable to fully inhibit the NTHi-induced expression of Group A-chemokines in the stable cell line overexpressing PDE4B2. Moreover, both PDE4B2-WT and PDE4B2-D392A (the mutant with no enzymatic activity) markedly enhanced the NF-κB promoter activity and Group A-chemokine expression, although PDE4B2-D392A enhanced NF-κB activation and chemokine expression to a lesser extent compared with PDE4B2-WT. It should also be noted that roflumilast (up to 10 µM) was unable to fully inhibit the IKKβ-CA-induced NF-κB promoter activity and Group A-chemokine expression in the cells overexpressing PDE4B2-WT or PDE4B2-D392A. Together, these results demonstrate that up-regulated PDE4B2 may contribute to the up-regulation of these chemokines in both enzymatic activity-dependent and -independent manners, thereby providing the evidence for the first time that PDE4B2 may act as a non-enzymatic adaptor protein in regulating the inflammatory response. Future studies are warranted to further elucidate the underlying mechanism.

The third major finding in the present study is that PKA-Cβ but not PKA-Cα is specifically required for mediating the synergistic induction of PDE4B2 and the resultant inflammatory response in human airway epithelial cells. Previously, it has been shown that PKA-Cα activates NF-κB signaling via phosphorylating p65 at Ser276 in a cAMP-independent manner (Zhong et al., *Cell*, 89(3):413-424, 1997). PKA-Cα has been shown to be maintained in an inactive state through association with IκB complex. Signals that lead to IκB degradation result in PKA-Cα activation and subsequent phosphorylation of p65 at Ser276. This previous study suggests that the cAMP-independent PKA activation mechanism is involved in NF-κB activation and inflammation in response to inflammatory stimuli such as LPS, mitogens, cytokines, and viruses. In the current study, we reported a distinct novel mechanism by which cAMP synergizes with NF-κB signaling to up-regulate PDE4B2 through PKA-Cβ but not PKA-Cα mediated phosphorylation of p65 at Ser276 in the contexts of the presence of both bacterial pathogen and cAMP-elevating agents. Future study is required to further determine whether PKA-Cα and PKA-Cβ specifically mediate the cAMP-independent and cAMP-dependent regulation of p65 phosphorylation, respectively.

In addition to the distinct roles of PKA-Cα and PKA-Cβ in regulating PDE4B2 expression, PKA-Cα and PKA-Cβ also appear to differentially modulate the expression of pro-inflammatory mediators. For example, we found that some of the NTHi-induced pro-inflammatory mediators were increased upon PKA-Cα knockdown, which is line with the anti-inflammatory role of PKA-Cα previously reported in other cell types (Ollivier et al., *J. Biol. Chem.*, 271(34):20828-20835, 1996). The role of PKA-Cβ in mediating the inflammatory response remains largely unclear. In this study, we found that the expression of pro-inflammatory mediators was reduced by PICA-Cβ knockdown, indicating the pro-inflammatory role of PICA-Cβ. These data suggest that PKA-Cβ-selective inhibition may represent a promising strategy to suppress pro-inflammatory mediators without compromising the anti-inflammatory effects mediated by PKA-Cα. Given the distinct roles of PKA-Cα and Cβ in regulating PDE4B2 and pro-inflammatory mediators, it is likely that PKA may be involved in regulating the physiological and pathological responses in an isoform-specific manner (Padmanabhan et al., *J. Biol. Chem.*, 288(20):14158-14169, 2013). Thus, special attention needs to be paid to the role of various isoforms of PKA for the studies aimed at determining the involvement of PKA.

The role and underlying mechanisms of PKA in regulating NF-κB signaling appears to be rather complex. In some model systems, the activation of PKA inhibits NF-κB nuclear translocation. For example, TNF-α mediated nuclear translocation of p65 is enhanced by PKA depletion using siRNA in HeLa cells (King et al., *PloS ONE*, 6(4): e18713, 2011). Forskolin impairs the nuclear translocation of p65 in Jurkat T-lymphocytes (Neumann et al., *EMBO J.*, 14(9):1991-2004, 1995). There are also NF-κB nuclear translocation-independent mechanisms. For example, in human monocytes and endothelial cells, cAMP inhibits NF-κB-mediated transcription without preventing the nuclear translocation of NF-κB complex. Instead, cAMP/PKA inhibits NF-κB-dependent transcriptional activity by phosphorylating CREB, which competes with p65 for limiting amounts of NF-κB co-activator CREB-binding protein (CBP) Parry and Mackman, *J. Immunol.*, 159(11):5450-5456, 1997). It has also been shown that the inhibitory action of the cAMP/PKA pathway on the transcriptional activity of NF-κB in Jurkat T-lymphocytes is exerted through directly or indirectly modifying the C-terminal transactivation domain of p65, which is independent of CREB and p65 phosphorylation at Ser276 (Takahashi et al., *Eur. J. Biochem.*, 269(18):4559-4565, 2002). All above-mentioned studies provide evidence for the inhibitory effect of cAMP/PKA on NF-κB transcriptional activity. However, there is also evidence that PKA is able to activate NF-κB signaling, in which phosphorylation of p65 at Ser276 appears to be critical. For example, phosphorylation of NF-κB at Ser276 by PKA stimulates NF-κB transcriptional activity by promoting the interaction of NF-κB with the co-activator CBP/p300 (Zhong et al., 1998, supra. NF-κB p65 phosphorylation at Ser276 by PKA activates NF-κB and contributes to the malignant phenotype of head and neck cancer (Arun et al., *Clin. Cancer Res.*, 15(19):5974-5984, 2009). It has been also shown that PKA-Cα activates NF-κB signaling via phosphorylating p65 at Ser276 in an IKKβ-dependent but cAMP-independent manner (Zhong et al., 1997, supra). In the present study, we show that PKA-Cβ also phosphorylates p65 at Ser276 but in a cAMP-dependent manner, which is critical for the synergistic induction of PDE4B2 by NTHi and roflumilast in bronchial epithelial cells. Taken together, these lines of experimental evidence suggest that cAMP and/or PKA can modulate NF-κB activation/inactivation via various mechanisms, which might be dependent upon cell types and sources of cAMP and PKA as well as the NF-κB subunits present in different signaling complexes. In addition, the expression levels of A kinase-interacting protein 1 (AKIP1) in various cell types or conditions also appear to be important for the effect of PKA on NF-κB activity. It has been shown that in cells with low levels of AKIP1, PKA-activating agents inhibit NF-κB transcriptional activity. In contrast, in cells with high levels of AKIP1, the PKA activation increases p65 phosphorylation at Ser276 and synergizes with NF-κB activation (Gao et al., *J. Biol. Chem.*, 285(36):28097-28104, 2010).

In summary, our studies provide novel insights not only into the molecular mechanism underlying the synergistic induction of PDE4B2 expression in the context of the complex pathogenesis and medications of COPD but also into the signaling cross-talk between PKA-Cβ and p65 via a cAMP-dependent manner. Our results also provide evidence for the first time that PDE4B2 may act, at least in part, as a non-enzymatic adaptor protein in regulating the inflammatory response. Combined administration of roflumilast with a PKA-Cβ-selective inhibitor (and/or the other inhibitors described herein) may help attenuate the unwanted up-regulation of PDE4B2, thereby representing a promising therapeutic strategy to improve the efficacy, decrease the effective dose and possibly ameliorate the tolerance of PDE4-inhibitors in patients with COPD exacerbation.

What is claimed is:

1. A method of treating chronic obstructive pulmonary disease (COPD), the method comprising administering an effective amount of roflumilast and an effective amount of a second agent to a patient having COPD, wherein the patient is infected with *Haemophilus influenzae*, wherein the second agent inhibits the upregulated activity or upregulated expression of phosphodiesterase 4B2 (PDE4B2) associated with roflumilast treatment and *Haemophilus influenzae* infection, and wherein the second agent is selected from the group consisting of a glucocorticoid; a hypoxia-inducible factor 1α (HIF-1α) inhibitor selected from the group consisting of chrysin, chetomin, 2-methoxyestradiol, cryptotanshinone, and 17-dimethylaminoethylamino-17-demethoxygeldanamycin (17-DMAG); curcumin; an alkenyldiarylmethane; a 2-arylpyrimidine; a triazine; a pyridazino[4,5-b]indolizine; a nucleic acid molecule that selectively inhibits the expression of PDE4B2; and combinations thereof.

2. The method of claim 1, wherein the roflumilast and the second agent are combined in single dosage form.

3. The method of claim 1, wherein the roflumilast and the second agent are administered concurrently or sequentially by the same or different routes of administration.

4. The method of claim 3, wherein the roflumilast is administered orally and the second agent is administered directly to the lungs.

5. The method of claim 3, wherein the second agent is formulated as a dry powder for administration directly to the lungs by inhalation.

6. The method of claim 1, wherein the glucocorticoid is selected from the group consisting of dexamethasone, cortisol, cortisone, prednisone, prednisolone, methylprednisolone, betamethasone, triamcinolone, beclometasone, fludrocortisone acetate, deoxycorticosterone acetate, and aldosterone.

7. The method of claim 1, wherein the HIF-1α inhibitor is 17-dimethylaminoethylamino-17-demethoxygeldanamycin (17-DMAG).

8. The method of claim 1, wherein the alkenyldiarylmethane is:

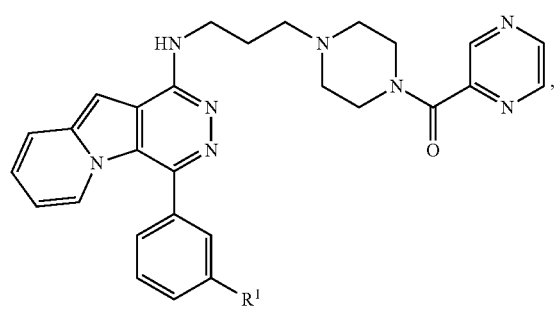

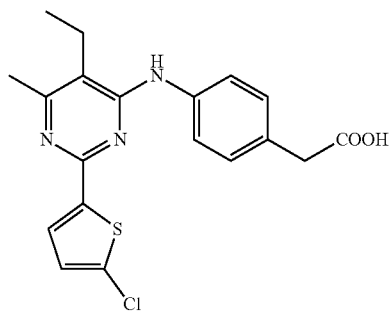 [SMILES: CCc1c(C)nc(-c2ccc(Cl)s2)nc1Nc1ccc(CC(=O)O)cc1]

or a pharmaceutically acceptable salt thereof.

9. The method of claim 1, wherein the 2-arylpyrimidine is:

or a pharmaceutically acceptable salt thereof.

10. The method of claim 1, wherein the triazine is a compound according to the formula:

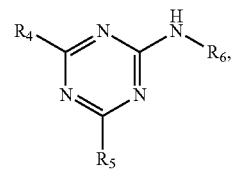

wherein each of $R_4$, $R_5$, and $R_6$ is selected from the group consisting of hydrogen, halogen, cyano, carboxyl, alkyl, aryl, or heterocycle and can be optionally substituted with one or more of halogen, cyano, carboxyl, alkyl, aryl, or heterocycle.

11. The method of claim 1, wherein the pyridazino[4,5-b]indolizine is a compound according the formula:

wherein $R^1$ is H or —$NO_2$,
or a pharmaceutically acceptable salt thereof.

* * * * *

UNITED STATES PATENT AND TRADEMARK OFFICE
CERTIFICATE OF CORRECTION

PATENT NO. : 11,045,456 B2
APPLICATION NO. : 15/559728
DATED : June 29, 2021
INVENTOR(S) : Jian-Dong Li It is certified that error appears in the above-identified patent and that said Letters Patent is hereby corrected as shown below:

In the Specification

Column 6, Lines 1-2:
Delete: "FIG. 8 is a representation of the mRNA sequence of human PDE4B (SEQ ID NO:1)."

Column 6, Lines 3-4:
Delete: "FIG. 9 is a representation of the nucleic acid sequence of a human PDE4B2 (SEQ ID NO:2)."

Column 6, Line 5:
Delete: "FIGS. 10A and 10B" and insert --"FIGS. 8A and 8B"--

Column 14, Lines 48-49:
Delete: "For easy reference, the mRNA sequence of human PDE4B is shown in FIG. 8." and insert --For easy reference, the mRNA sequence of human PDE4B is listed as SEQ ID NO: 1 in the attached Sequence Listing.--

Signed and Sealed this
Twenty-fourth Day of January, 2023

Katherine Kelly Vidal
*Director of the United States Patent and Trademark Office*